(12) United States Patent
Shackney

(10) Patent No.: US 7,412,333 B2
(45) Date of Patent: Aug. 12, 2008

(54) METHOD FOR PROGNOSTIC FACTOR ANALYSIS REGARDING CANCERS

(75) Inventor: Stanley E. Shackney, Mt. Lebanon, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 10/178,083

(22) Filed: Jun. 22, 2002

(65) Prior Publication Data

US 2002/0198664 A1 Dec. 26, 2002

Related U.S. Application Data

(60) Provisional application No. 60/300,921, filed on Jun. 26, 2001.

(51) Int. Cl.
*G01N 33/48* (2006.01)
*G06F 19/00* (2006.01)
(52) U.S. Cl. .................... 702/19; 702/21; 435/7.23; 436/64; 703/11
(58) Field of Classification Search .................. 702/19, 702/21; 435/4; 436/63, 64; 514/1
See application file for complete search history.

(56) References Cited

U.S. PATENT DOCUMENTS 5,989,811 A * 11/1999 Veltri et al. ................ 435/6

OTHER PUBLICATIONS

Stanley E. Shackney et al., "Origins and Clinical Implications of Aneuploidy in Early Bladder Cancer,"Cytometry (Communications in Clinical Cytometry), Wiley-Liss, Inc., No. 22, p. 307-316, (May 1, 1995).
Stanley E. Shackney et al., "The Accumulation of Multiple Genetic Abnormalities in Individual Tumor Cells in Human Breast Cancers: Clinical Prognostic Implications," The Cancer Journal, Scientific American, Inc., vol. 2 (No. 2), p. 105-114, (Mar. 1, 1996).
Stanley E. Shackney et al., "Aneuploidy in Breast Cancer: A Fluorescence In Situ Hybridization Study," Cytometry (Communications in Clinical Cytometry), Wiley-Liss, Inc., No. 22, p. 282-291, (Mar. 7, 1995).
Charles A. Smith et al., "Correlations Among p53, Her-2/neu, and ras Overexpression and Aneuploidy by Multiparameter Flow Cytometry in Human Breast Cancer: Evidence for a Common Phenotypic Evolutionary Pattern in Infiltrating Ductal Carcinomas," Clinical Cancer Research, p. 112-126, (Jan. 1, 2000).
Stanley E. Shackney et al., "Intracellular Coexpression of Epidermal Growth Factor Receptor, Her-2/neu, and p21 ras in Human Breast Cancers: Evidence for the Existence of Distinctive Patterns of Genetic Evolution That Are Common to Tumors from Different Patients," Clinical Cancer Research, p. 913-928, (Apr. 1, 1998).
Stanley E. Shackney et al., "Common Patterns of Genetic Evolution in Human Solid Tumors," Cytometry, Wiley-Liss, Inc., p. 1-27, (May 11, 1997).
Stanley E. Shackney et al., "Genetic Evolutionary Staging of Early Non-Small Cell Lung Cancer: The P53<HER-2/NEU>RAS Sequence," The Journal of Thoracic and Cardiovascular Surgery, vol. 118 (No. 2), p. 259-269, (Aug. 1, 1999).
Laura E. Janocko et al., "Distinctive Patterns of Her-2/Neu, c-myc, and Cyclin D1 Gene Amplification by Fluorescence In Situ Hybridization in Primary Human Breast Cancers," Cytometry (Communications in Clinical Cytometry), Wiley-Liss, Inc., p. 136-149, (2001).
Stanley E. Shackney et al., "Intracellular Patterns of Her-2/neu, ras, and Ploidy Abnormalities in Primary Human Breast Cancers Predict Postoperative Clinical Disease-Free Survival," Clinical Cancer Research, p. 3042-3052, (May 1, 2004).
Stanley E. Shackney et al., "Molecular Evolutionary Patterns in Breast Cancer," Advances in Anatomic Pathology, Lippincott Williams & Wilkins (USA), vol. 10 (No. 5), p. 278-290, (Sep. 2003).

* cited by examiner

*Primary Examiner*—Carolyn Smith
(74) *Attorney, Agent, or Firm*—Ansel M. Schwartz

(57) ABSTRACT

A method for treating a patient with cancer includes the steps of obtaining cells from a cancerous tumor in the patient. Then there is the step of performing multiple correlated measurements on each cell to obtain cell data for each cell regarding each cell's place in a genetic evolutionary pathway that had occurred in the tumor. Next there is the step of determining from the cell data a likelihood of recurrence of the cancer by minimizing false negatives. A method for treating a patient with cancer. The method includes the steps of obtaining cells from a cancerous tumor in the patient. Then there is the step of obtaining cell data for each cell regarding each cell's place in a genetic evolutionary pathway that had occurred in the tumor. Next there is the step of recognizing distinctive false negative patterns from the cell data. Then there is the step of correlating the false negative patterns to aberrations in mitogenic signaling to determine a likelihood of recurrence of the cancer in the patient. An apparatus for treating a patient with cancer.

1 Claim, 12 Drawing Sheets

METHOD FOR PROGNOSTIC FACTOR ANALYSIS REGARDING CANCERS

This application claims the benefit of U.S. Provisional Application(s) No(s).: 60/300,921 Jun. 26, 2001

FIELD OF THE INVENTION

The present invention is related to the likelihood of the reoccurrence of cancer in a patient. More specifically, the present invention is related to the likelihood of the reoccurrence of cancer in a patient by minimizing false negatives and false positives.

BACKGROUND OF THE INVENTION

Of the 180,000 new cases of breast cancer that are diagnosed annually in the United States, approximately 140,000 will have no clinical evidence of metastatic disease. Almost all of these patients are candidates for adjuvant chemotherapy, hormonal therapy, or both. Yet, 70,000-75,000 of the 100,000 patients without axillary node involvement and 12,000-15,000 of the 40,000 patients with axillary node involvement, would remain free of disease for the remainder of their lives even without adjuvant treatment. If the 90,000 patients who are actually cured with local therapy could be identified with confidence, they could be spared unnecessary treatment, and the health care system could be spared an unnecessary expenditure that can be estimated to exceed 500 million dollars annually (assumed treatment cost per patient in the range of $5,000-$10,000).

Although many statistically significant prognostic factors have been identified in breast cancer, no single factor has been found to date that can separate patients who are likely to relapse from those who are likely to remain disease-free cleanly enough for making clinical therapeutic decisions. For example, the presence of tumor cells in the bone marrow has recently been found to correlate very well (P<0.001) with subsequent recurrences that involve bone, but not with locoregional or purely visceral recurrences (1). One might wish to combine prognostic factors empirically to achieve a better separation between patients who are likely to develop tumor recurrences from those who are not; indeed, the combination of axillary nodal status and the presence or absence of tumor cells in the marrow appears promising (1). However, the empirical approach is by its very nature haphazard and inefficient, and seems unlikely to produce results that would be universally accepted as definitive.

The premises underlying the invention herein are that progress in the application of prognostic factors in breast cancer will ultimately depend on the intelligent use of such factors in combination, that the most robust combinations of prognostic factors are likely to be those that are based on biological relationships at the molecular level.

This approach has been 1) to determine critical sequences of genetic evolutionary changes in breast cancer that are responsible for increasing tumor aggressiveness, in order to establish how far a given tumor has progressed in its genetic evolutionary sequence, 2) to determine if a given tumor has undergone the critical steps in the sequence that are necessary for cellular acquisition of the capacity to metastasize, and 3) to apply this information clinically for purposes of prognosis and adjuvant treatment planning.

The underlying principle that guided the work described herein was that the increase in tumor aggressiveness that accompanied tumor progression was the result of an accumulation of genetic abnormalities within individual cells. This was confirmed by studies in which multiple correlated measurements on each cell in each tumor sample were performed by means of multiparameter flow cytometry (FCM), by multiparameter fluorescence in situ hybridization (FISH) studies, and, more recently, by laser scanning cytometry (LSC). Patients have been followed prospectively to assess the biological consequences and clinical outcomes of the patterns of intracellular geno-phenotypic abnormalities that were found in the cells of their primary tumors at the time of surgery. Early studies showed that the accumulation of aneuploidy, Her-2/neu overexpression and ras overexpression in the same cells (triple positive cells) was of prognostic significance in breast cancer (2). These ongoing studies have recently been updated, and the prognostic information conveyed by the intracellular accumulation of these three abnormalities has been found to be of even greater statistical significance after up to 10 years of follow-up.

It has been found that the commonly observed pattern of aneuploidy, Her-2/neu overexpression and ras overexpression was characteristic of approximately two thirds of p53-dysfunctional, non-lobular breast cancers (chiefly infiltrating ductal tumors), whereas the characteristics of lobular tumors (representing ~10 percent of the total), and those of the remaining one third of the p53-dysfunctional, diploid non-lobular breast cancers were quite different (3-5). Studies have also indicated that within individual tumors the development of p53 dysfunction generally occurs before the development of Her-2/neu overexpression, and that ras overexpression is a late event (4). Based on these findings, it was concluded that the majority of non-lobular breast cancers follow an evolutionary pathway in which wild type p53 function must be abrogated before sustained receptor tyrosine kinase-induced, ras-mediated mitogenic signaling can proceed unimpeded. The fact that p53 abnormalities, aneuploidy, Her-2/neu amplification/overexpression, and ras overexpression can all be found in ductal carcinomas in situ (DCIS), a preinvasive and pre-metastatic stage of breast cancer, suggests that these changes herald subsequent evolutionary pathway-specific abnormalities that are more directly responsible for the acquisition of metastatic potential.

A major factor that constrained the clinical application of these findings in the past was the presence of false negative tumors (tumors that did not contain detectable proportions of triple positive cells, but recurred nevertheless). The false negative rate, which was in the range of 10 percent, had to be reduced substantially before this approach could be used to identify specific patients who are at such low risk for recurrence that adjuvant therapy can safely be withheld. In studies, the false negative tumors could be assigned to one of four groups, based on the patterns of intracellular abnormalities that they contained. An orderly strategy has been adapted for identifying combinations of molecular abnormalities within each of these groups that would distinguish patients at high risk for recurrence from those who are at low risk. This strategy is at the heart of the technique herein, since it assures that one can reduce the prognostic false negative rate progressively, until a level is reached that is acceptable for clinical application, no matter what that level might be. Then, aggressive therapy can be applied to patients at high risk for the presence of occult disease or micromatastesis. While much of the work to date has been carried out in breast cancer and lung cancer, the principles underlying this approach are applicable to all types of human solid tumors.

SUMMARY OF THE INVENTION

The present invention pertains to a method for treating a patient with cancer. The method comprises the steps of obtaining cells from a cancerous tumor in the patient. Then there is the step of performing multiple correlated measurements on each cell to obtain cell data for each cell regarding each cell's place in a genetic evolutionary sequence or pathway that had occurred in the tumor. Next there is the step of determining from the cell data a likelihood of recurrence of the cancer by minimizing false negatives.

The present invention pertains to a method for treating a patient with cancer. The method comprises the steps of obtaining cells from a cancerous tumor in the patient. Then there is the step of obtaining cell data for each cell regarding each cell's place in a genetic evolutionary sequence that had occurred in the tumor. Next there is the step of recognizing distinctive false negative patterns from the cell data. Then there is the step of correlating the false negative patterns to aberrations in mitogenic signaling to determine a likelihood of recurrence of the cancer in the patient.

The present invention pertains to an apparatus for treating a patient with cancer. The apparatus comprises means for obtaining cell data from cells of a cancerous tumor in the patient to obtain cell data for each cell regarding each cell's place in a genetic evolutionary sequence that has occurred in the tumor. The apparatus comprises means for determining from the cell data a likelihood of recurrence of the cancer by minimizing false negatives.

The present invention pertains to a method for treating a patient with cancer. The method comprises the steps of obtaining cells from a cancerous tumor in the patient. Then there is the step of performing multiple correlated measurements on each cell to obtain cell data for each cell regarding each cell's place in a genetic evolutionary sequence that had occurred in the tumor. Next there is the step of determining from the cell data a likelihood of recurrence of the cancer by minimizing false positives.

BRIEF DESCRIPTION OF THE DRAWINGS

In the accompanying drawings, the preferred embodiment of the invention and preferred methods of practicing the invention are illustrated in which.

DETAILED DESCRIPTION

Figure 13:
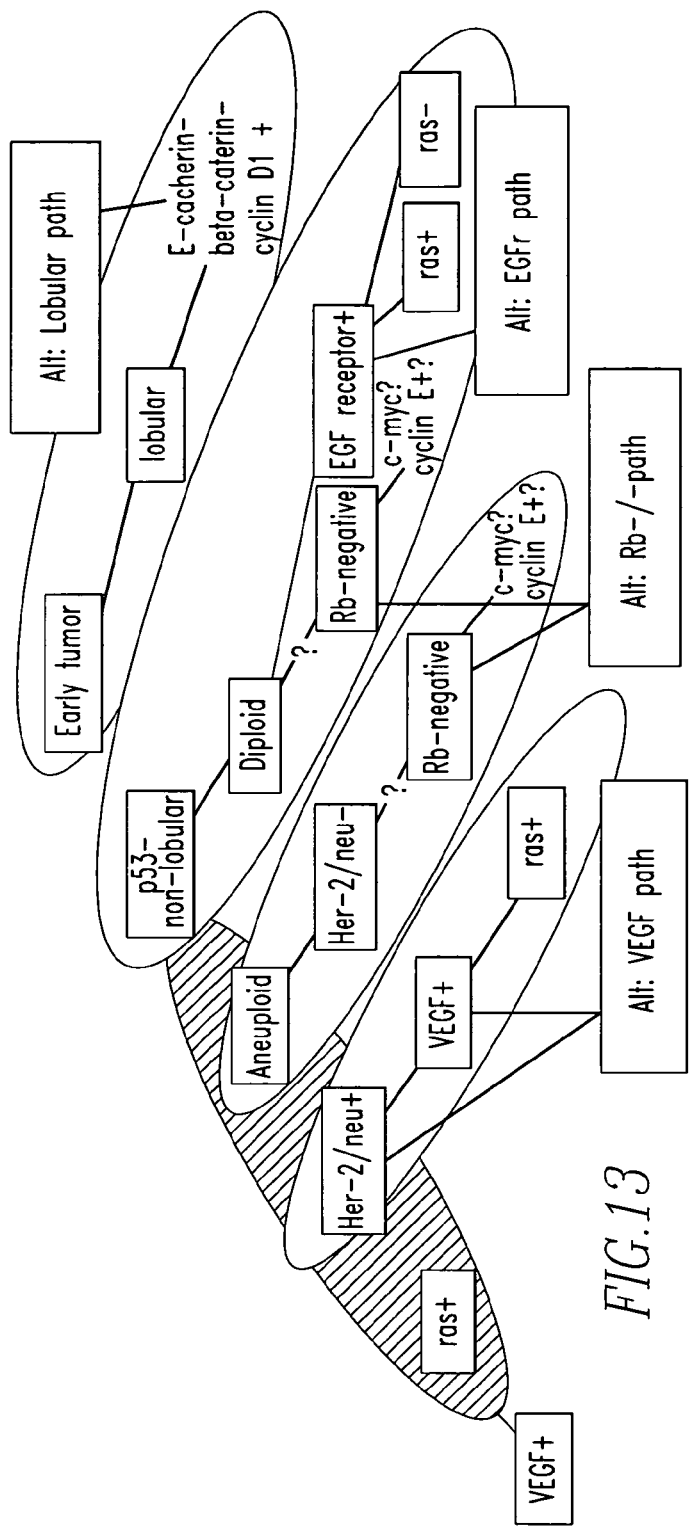
FIG. 13 shows a branching evolutionary tree for human breast cancer.
Figure 14:
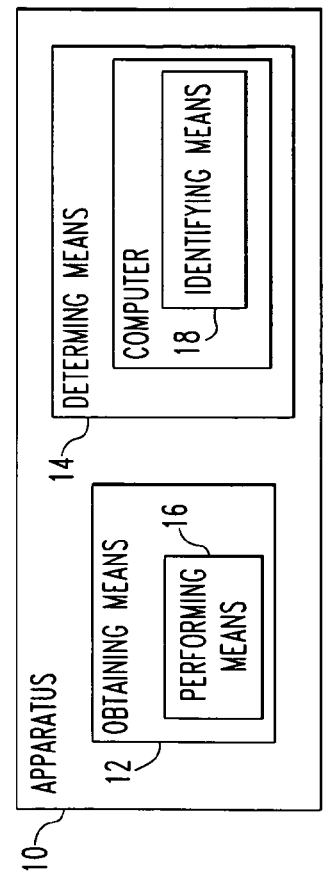
FIG. 14 is a schematic representation of the apparatus of the present invention.

Referring now to the drawings wherein like reference numerals refer to similar or identical parts throughout the several views, and more specifically to FIG. 13 thereof, there is shown an apparatus 10 for treating a patient with cancer. The apparatus comprises means 12 for obtaining cell data from cells of a cancerous tumor in the patient to obtain cell data for each cell regarding each cell's place in a genetic evolutionary sequence that has occurred in the tumor. The apparatus 10 comprises means 14 for determining from the cell data a likelihood of recurrence of the cancer by minimizing false negatives.

Preferably, the obtaining means 12 includes means 16 for performing multiple correlated measurements on cells from the tumor to obtain the cell data for each cell regarding each cell's place in the genetic evolutionary sequence that has occurred in the tumor. The performing means 16 for performing multiple correlated measurements on each cell in each tumor sample can be accomplished, for instance, by multiparameter flow cytometry (FCM), by multiparameter fluorescence in situ hybridization (FISH) studies, and by laser scanning cytometry (LSC); all of which are well known to one skilled in the art.

The determining means 14 preferably includes means 18 for identifying abnormalities in a cell. Preferably, the identifying means 18 identifies how many abnormalities are present in each cell. The identifying means 18 preferably identifies which type of abnormality each abnormality is. Preferably, the determining means 14 determines if greater than 5 percent of the cells have three abnormalities. The determining means 14 preferably determines from the cell data a likelihood of recurrence of the cancer by minimizing false positives.

The present invention pertains to a method for treating a patient with cancer. The method comprises the steps of obtaining cells from a cancerous tumor in the patient. Then there is the step of performing multiple correlated measurements on each cell to obtain cell data for each cell regarding each cell's place in a genetic evolutionary sequence that had occurred in the tumor. Next there is the step of determining from the cell data a likelihood of recurrence of the cancer by minimizing false negatives.

Preferably, the determining step includes the step of utilizing survival curves to determine the likelihood of recurrence of the cancer. The determining step preferably includes the step of minimizing false positives.

Preferably, the step of obtaining cells includes the step of obtaining cells from a solid cancerous tumor. The step of obtaining cells preferably includes the step of obtaining cells from a cancerous tumor in the breast of the patient. Alternatively, the step of obtaining cells includes the step of obtaining cells from a cancerous tumor in the lung of the patient. The step of obtaining cells preferably includes the step of obtaining cells from sputum of the patient.

Preferably, after the determining step, there is the step of applying a therapy to the patient if it is determined there is a high likelihood of recurrence of the cancer. Alternatively, after the determining step, there is preferably the step of withholding therapy to the patient if it is determined there is no or a low likelihood of recurrence of the cancer.

The present invention pertains to a method for treating a patient with cancer. The method comprises the steps of obtaining cells from a cancerous tumor in the patient. Then there is the step of obtaining cell data for each cell regarding each cell's place in a genetic evolutionary sequence that had occurred in the tumor. Next there is the step of recognizing distinctive false negative patterns from the cell data. Then there is the step of correlating the false negative patterns to aberrations in mitogenic signaling to determine a likelihood of recurrence of the cancer in the patient.

Preferably, the step of obtaining cell data includes the step of performing multiple correlated measurements on each cell to obtain the cell data for each cell regarding each cell's place in the genetic evolutionary sequence that had occurred in the tumor.

The present invention pertains to a method for treating a patient with cancer. The method comprises the steps of obtaining cells from a cancerous tumor in the patient. Then there is the step of performing multiple correlated measurements on each cell to obtain cell data for each cell regarding each cell's place in a genetic evolutionary sequence that had occurred in the tumor. Next there is the step of determining from the cell data a likelihood of recurrence of the cancer by minimizing false positives.

In the operation of the invention, previous studies have shown that one can perform multiple cell-based measurements on human tumors and identify preferred sequences of geno-phenotypic changes. Preliminary analysis of the breast cancer data published in 1996 showed that these sequential changes were of clinical prognostic significance. Clinical follow up data confirmed early findings even more strongly, and also showed that The sequence, p53->Her-2/neu-> ras occurred early, just prior to the acquisition of metastatic potential, There were several distinctive patterns of false negative cases (cases that did not contain the p53->Her-2/neu-> ras sequence but still recurred)

It was recognized that the distinctive patterns that characterized the false negative cases represented alternative evolutionary pathways that could be related to physiologic aberrations in mitogenic signaling pathways that are based on known abnormalities in intracellular signaling molecules in cancer. The recognition of the distinctive false negative patterns, and the ability to correlate them to aberrations in mitogenic signaling form the basis for the strategy for minimizing false negatives in prognostic factor analysis. The same strategy can be used to minimize false positives, as well. That is, false positives arise when the prognostic factors being measured are necessary but not sufficient to produce metastases but when the changes responsible for sufficiency have not yet occurred. For example, suppose that the p53->Her-2/neu-> ras sequence required yet another unmeasured step, X, for the tumor cells to achieve metastatic potential. That is, suppose that the critical sequence for acquisition of metastatic potential is p53->Her-2/neu-> ras->X, and that most tumors that went on to relapse that had cells with p53, Her-2/neu, and ras abnormalities, also had to have had the unmeasured X abnormality for relapse to occur. Then, those few tumors in which the p53->Her-2/neu-> ras abnormalities occurred but in which the X abnormality had not yet occurred, would not relapse. These are false positive cases. The strategy for identifying these cases is to search for molecular species that meet the requirement for X, based on what is known about molecular signaling pathways and their aberrations. Once X is known, then the relapsers could be separated cleanly from the non-relapsers along the p53->Her-2/neu->ras->X pathway simply by including X among the other measurements.

At the heart of executing the strategy for minimizing false positive and false negative cases for prognostic purposes is the performance of multiple measurements per cell on large numbers of cells, and extracting information from the intracellular patterns of abnormalities in these measurements in order to identify early abnormalities by the fact that they can occur alone in persistent precursors, and late abnormalities by the fact that they occur together with accumulated early abnormalities in the same cells. This is unique with regard to using multiple (greater than 2) intracellular correlations for establishing genetic evolutionary sequences in human tumors, and relating them to prognosis.

The principle that has guided the approach to resolving the prognostic fates of false negative tumors is that they must follow alternative evolutionary pathways to the aneuploidy-> Her2/neu overexpression-> ras overexpression pathway, that are either separate, or that branch off from the main pathway prior to the development of ras overexpression. For example, one of the subsets of tumors that can generate false negative cases is characterized by aneuploidy, but no Her-2/neu or ras overexpression. If receptor tyrosine kinase and/or ras-mediated signaling is required primarily for cyclin D/cdk4 kinase-induced Rb phosphorylation and inactivation, (discussed more extensively below), then abnormalities in Her-2/neu and/or ras overexpression would be irrelevant in aggressive Rb negative tumors. Tumors characterized by aneuploidy and Her-2/neu overexpression, but no ras overexpression can also generate false negative cases. The studies indicate that VEGF overexpression in aneuploid cells often lies downstream of Her-2/neu overexpression and upstream of ras overexpression. Thus, VEGF, a known prognostic factor in breast cancer, participates in an alternative pathway consisting of aneuploidy-> Her-2/neu overexpression-> VEGF, which accounts for a substantial proportion of the cases that are false negative with respect to the aneuploidy-> Her-2/neu overexpression-> ras pathway.

The framework for identification and analysis of tumor evolutionary pathways is now described. The approach to prognostic factor studies has been greatly facilitated by several recent developments. First, it has become increasingly apparent that there are specific patterns of molecular abnormalities that occur in individual tumors that are recapitulated in tumors from different patients (described more fully below), and that these patterns are of clinical prognostic value. These patterns make it possible to correlate generic derangements in intracellular molecular network behavior that involve multiple molecular species with their clinical effects on tumor aggressiveness. However, there are special difficulties in determining these patterns in clinical samples: a) the material available for study is limited in quantity, and b) there is extensive clonal heterogeneity within clinical tumor samples. Recent advances in laser scanning cytometry (LSC), a newly emerging technology that is especially well suited for the analysis of tumor cells in clinical samples, have gone far to alleviate these difficulties, as described more fully below.

In regard to patterns of geno-phenotypic abnormalities in human tumors, and their relationships to intracellular molecular signaling networks, among the different types of patterns of molecular abnormalities that have been found in human tumors, two are focused on: the preferential clustering of geno-phenotypic changes in specific tumor subtypes, and preferred temporal sequences of occurrence of geno-phenotypic changes that are members of such clusters. There are distinctive clusters of geno-phenotypic abnormalities that occur within individual tumors, and are common to other tumors of similar type or subtype (7-11). Human colon cancers can be subdivided into a group of predominantly diploid, right sided tumors that often exhibit microsatellite instability (12) and mutations of the TGFb type II receptor and hMLH1 or hMSH2 genes, but rarely exhibit p53 abnormalities, and a group of predominantly left sided tumors that often exhibit structural and numerical chromosomal instability, but not microsatellite instability, and frequently exhibit p53 abnormalities (reviewed in (9)). In human breast cancer, p53 abnormalities, aneuploidy, amplification/overexpression of Her-2/neu, and c-myc amplification have been found to cluster in infiltrating ductal carcinomas (4), but these abnormalities do not occur frequently in lobular breast cancers, either alone or in combination (5).

Within specific clusters of geno-phenotypic abnormalities, certain abnormalities have been shown to occur in a preferred order in relation to other members of the cluster (13), and in relation to early or late clinicopathologic stages of disease (7, 10, 13-15). In studies of patients with Barrett's esophagus, for example, p53 abnormalities were found to appear early, in pre-dysplastic diploid cells. During the course of evolution from the premalignant state to invasive disease, tumors with p53 abnormalities were found to progress through an intermediate stage of tetraploidy (16) to gross aneuploidy (17-19). A similar sequence of events has been reported in individual human colon cancers (20, 21).

Figure 1:
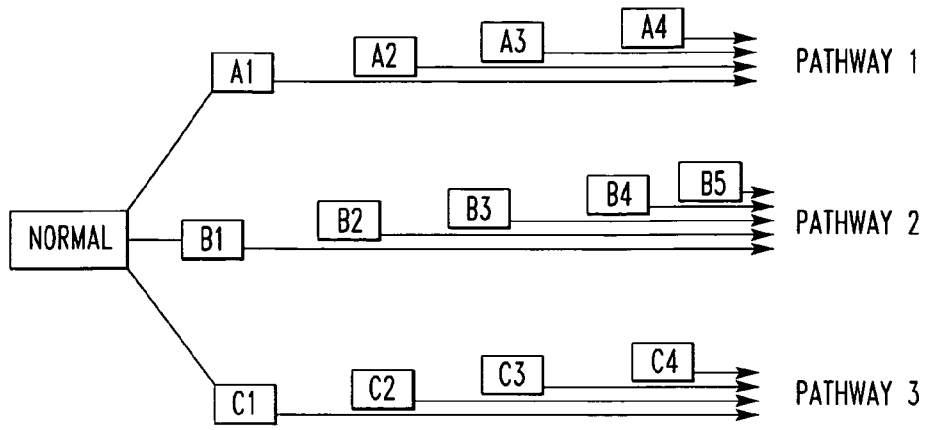
FIG. 1 shows a branching evolutionary model for human solid tumors, in which several different pathways can lead to the acquisition of metastatic potential.

FIG. 1 shows a branching evolutionary model for human solid tumors, in which several different pathways can lead to the acquisition of metastatic potential and illustrates a simple general model that embodies these observations. The clustering of geno-phenotypic abnormalities in individual tumors, and the common finding of the same clusters of abnormalities that accumulate in different tumors of the same type or subtype suggest that the same basic genetic evolutionary pathways may be recapitulated in different tumors. However, the observation that there are several different common clustering patterns would suggest that a given tumor might follow any one of several different evolutionary pathways as it progresses to increasingly more aggressive malignancy. One might expect that individual genetic abnormalities that confer an evolutionary survival benefit would persist, and accumulate in each of the most advanced cells in a tumor. For example, if the development of a p53 mutation results in genetic instability, then the late descendants of the cell that first developed the p53 mutation would each be expected to contain the mutant p53 gene plus whatever other mutant p53-induced genetic abnormalities that had been acquired. The model shown in FIG. 1 suggests that the patterns of intracellular accumulation of multiple geno-phenotypic abnormalities might provide a wealth of useful biological information in the study of human tumors, provided, that the tumor cells are preserved intact, and provided that one is able to perform multiple correlated measurements on each cell. It is here that the potential technological advantages of laser scanning cytometry come to the fore, as will be described below.

Figure 2:
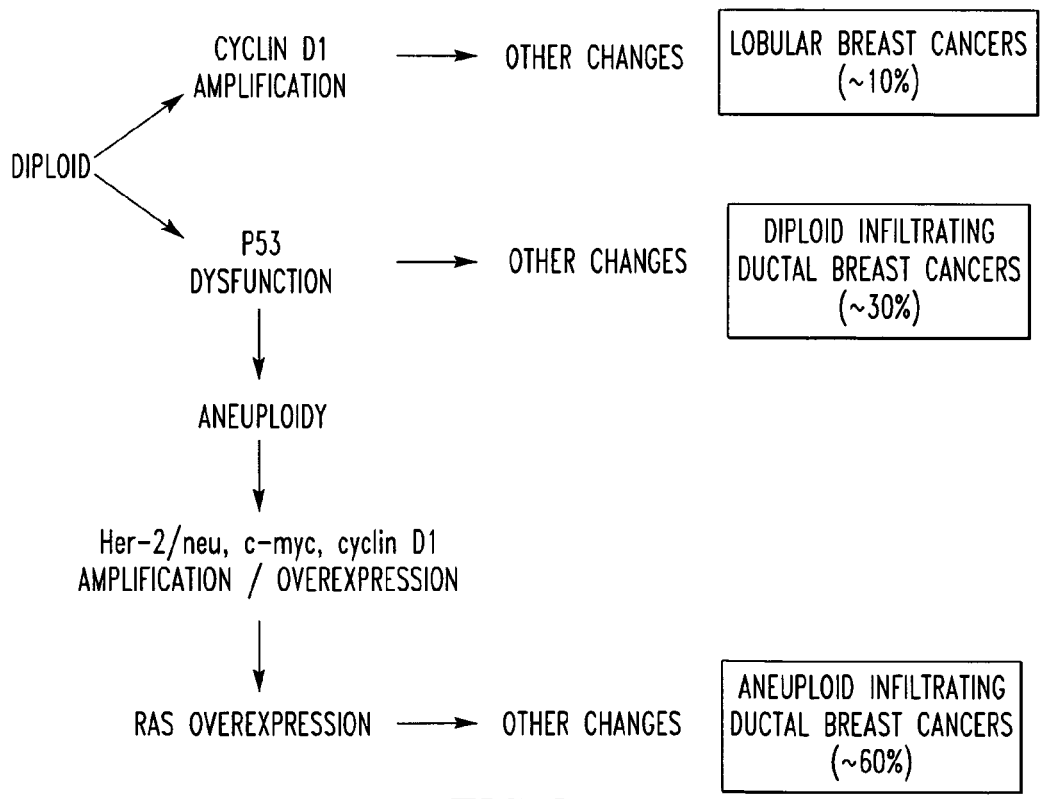
FIG. 2 shows evolutionary pathways identified in human breast cancers.

Much of the work to date in human breast cancer has been performed using intact cell-based measurements by multiparameter flow cytometry, fluorescence in situ hybridization (FISH), and, most recently, laser scanning cytometry (LSC). The results of studies completed to date are summarized in FIG. 2 which shows evolutionary pathways identified in human breast cancers. In brief, it has been found that cyclin D1 amplification can occur early in the course of tumor development, even prior to the evolutionary divergence of lobular breast cancers from non-lobular cancers (5). p53 dysfunction is a characteristic feature of infiltrating ductal breast cancers (4, 5) that occurs at a relatively early stage of tumor development, commonly appearing in diploid tumors prior to the development of Her-2/neu amplification (5) or overexpression (4), and prior to the development of ras overexpression (4). The frequencies been shown to increase progressively with increasing aneuploidy. Early amplification of c-myc is an especially prominent feature of hypertetraploid tumors (5).

Overall, human breast cancers appear to follow one of three major common evolutionary pathways. In about 60 percent of tumors, mostly infiltrating ductal carcinomas, the most advanced cell subpopulation (which typically represents 5-10 percent of the cells in any given tumor) consists of cells that exhibit p53 dysfunction (p53 allelic loss, p53 protein overexpression, or both) and aneuploidy, and that have also frequently accumulated such abnormalities as c-myc amplification, Her-2/neu amplification/overexpression, and cyclin D1 amplificaton cancers (4, 5). Since almost all of these abnormalities will have accumulated during preinvasive stages of disease (22), one might presume that their prognostic value is due to their status as obligatory antecedents to other geno-phenotypic abnormalities that develop during invasive stages of disease, that are more directly responsible for the acquisition of metastatic potential.

About 30 percent of breast cancers are infiltrating ductal carcinomas that commonly exhibit p53 dysfunction, but remain diploid cancers (4, 5). Her-2/neu, c-myc, and cyclin D1 amplification are relatively uncommon in these cancers (5). It has been found that in diploid breast cancers, intracellular levels of EGF receptor commonly equal or exceed the levels of Her-2/neu protein in the same cells, whereas in aneuploid tumors, and particularly in the aneuploid cell components of aneuploid tumors, the level of Her-2/neu protein is often much higher than that of EGF receptor in the same cells (3). It has also been noted that intracellular levels of EGF receptor and levels of ras protein in the same cells are closely correlated, independently of intracellular levels of Her-2/neu protein in the same cells (3). However, in diploid non-lobular breast tumors, little is known about the specific geno-phenotypic abnormalities that lie downstream of p53 dysfunction in the evolutionary pathway, that are responsible for invasiveness and the acquisition of metastatic potential.

Approximately 10 percent of human breast cancers are classified as lobular tumors. Lobular breast cancers often lack many of the molecular abnormalities that are characteristic of infiltrating ductal carcinomas, except for cyclin D1amplification. Lobular breast cancers are usually diploid (23); they do not often exhibit p53 abnormalities (reference (5); also see (9)), Her-2/neu abnormalities (reference (5); also reviewed in (9), or c-myc abnormalities (references (5), (24, 25)). Lobular breast cancers also have lower S fractions than non-lobular breast cancers, (4), and, unlike many non-lobular breast cancers, they generally retain estrogen receptor (26). Truncating mutations of the E-cadherin gene have been found in many lobular breast cancers, but not in ductal carcinomas (27). The absence of E-cadherin protein expression is a characteristic feature of lobular breast cancers, (28-30), but not of infiltrating ductal cancers, where E-cadherin protein expression is often reduced but rarely absent (28-30). Interestingly, in lobular cancers, reduced expression of b-catenin often accompanies loss of E-cadherin expression in the same tumor. Whether loss of E-cadherin, reduced expression of b-catenin, and/or cyclin D1amplification/overexpression are among the critical abnormalities that drive tumor progression in lobular breast cancers remains to be determined.

How can such information be used to improve clinical prognostic capabilities? First, even on purely empirical grounds, knowing which evolutionary pathway is being followed by a given tumor can be helpful in choosing prognostic factors that are relevant, and excluding irrelevant prognostic factors from consideration. Thus, for example, p53 dysfunction, c-myc amplification, Her-2/neu amplification/overexpression, S fraction, or the loss of estrogen receptor might be of no value in determining prognosis in lobular breast cancers, since even those lobular breast cancers that recur may not exhibit these abnormalities. Conversely, when assessing the potential value of these factors in human breast cancer, it is useful to systematically exclude lobular tumors from the analysis, since their behavior would only obscure the overall results in non-lobular tumors with respect to these factors.

Going a step further, one expects that for many of the geno-phenotypic abnormalities under consideration, additive or synergistic interactions that might contribute to increasing tumor aggressiveness would occur only when these abnormalities accumulate in the same cells. It has previously been shown that patients with primary breast cancers in which aneuploidy, Her-2/neu overexpression and ras overexpression were present in the same cells were more likely to have tumor recurrences than patients whose tumors contained fewer abnormalities in the same cells, or whose tumors exhibited all three abnormalities in different cells (2). This study has recently been updated, and the data show even larger statistically significant differences after up to nearly 10 years of follow-up.

The model shown in FIG. 1 suggests that the most effective combination of prognostic factors for a given tumor might consist of measurements of geno-phenotypic abnormalities that are useful in determining which evolutionary pathway is being followed by that tumor, coupled with measurements of the downstream abnormalities that are likely to be most closely linked with, and possibly responsible for the development of the metastatic phenotype in that pathway.

The approach has been adapted for the elucidation of these evolutionary pathways and the identification of their downstream components that is based on the general premise that each of the common genetic evolutionary pathways in human breast cancers represents a sequence of abnormalities that starts with a breach in one of several universal points of vulnerability in the system of biological checks and balances that is embedded in the intracellular molecular signaling network of normal cells. Once breached, this protective system undergoes a series of progressive degradative changes, the specifics of which (nature, timing, and sequence) are presumably constrained by the 'hard wired' characteristics of the system itself.

Figure 3:
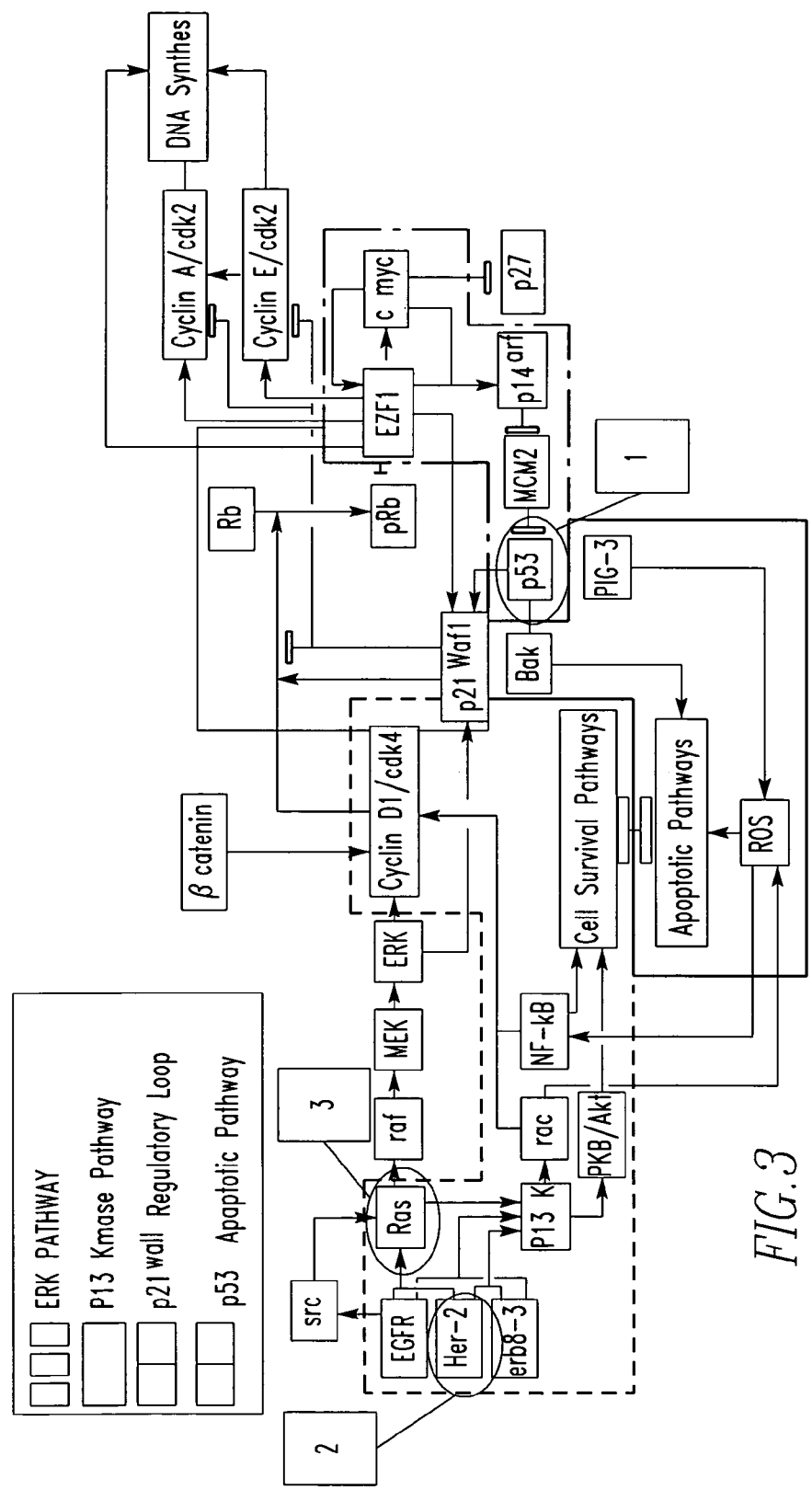
FIG. 3 shows a model for relating the non-lobular aneuploid evolutionary sequence to intracellular mitogenic signaling pathways.

FIG. 3 shows a model for relating the non-lobular aneuploid evolutionary sequence to intracellular mitogenic signaling pathways. The ERK and PI3 kinase mitogenic signaling pathways converge on cyclin D1, phosphorylate Rb, enabling E2F and c-myc induction and the gereration transcriptional activity that leads to DNA synthesis. E2F1 and p53 participate in a G1 autoregulatory feedback loop that is governed by the level of p21Waf1. They are also members of a coupled circuit that balances apoptosis and ras-mediated cell survival signals. The early development of p53 dysfunction has at least four related proliferative dysregulatory consequences: a) abrogation of p53mediated apoptosis, b) impaired elimination of numerical and structural chromosomal abnormalities, leading to the accumulation of aneuploid cells with frequent gene amplification, c) the development of Her-2/neu amplification, and d) the activation of unregulated ras-mediated mitogenic signaling.

In regard to tumor evolutionary sequences and the behavior of intracellular molecular networks, early reports (circa 1994-95) of clustering of abnormalities involving molecular components of mitogenic signaling pathways showed that cyclin D1amplification/overexpression and/or loss of p16Ink4a are common in human solid tumors with intact Rb, but not in tumors in which Rb protein was lost (31-37). It was surmised that these molecular species were all members of a single intracellular pathway that involved Rb as a downstream component (36). The results of extensive mechanistic studies in experimental cell systems in the last several years have suggested that this Rb pathway is, itself, but one component of a highly complex set of interlocking feedback loops, and that Rb itself actively participates in regulating cyclin D1levels (38). Cyclin D1, in complexes with cdk4 or cdk6, has been identified as having a major role in phosphorylating and inactivating Rb, thereby blocking its inhibition of function of the family E2F transcription factors (reviewed in (39, 40)). Members of the E2F family, chiefly E2F1, together with c-myc, play major roles both in the initiation of DNA synthesis and the induction of apoptosis (41)).

Cyclin D1has emerged as a point of convergence for a number of different upstream mitogenic signaling pathways (42, 43) (FIG. 3). These include ras-mediated pathways (42) of which the raf/MEK/ERK pathway and the PI3 kinase pathway are the best studied, and, interestingly, a b-catenin-mediated pathway that has recently been identified in colon cancer cells (44, 45). The focus is primarily on the ERK- and PI3 kinase pathways. Many of the known components of the ERK and PI3 kinase pathways have been implicated in ras-mediated neoplastic transformation in experimental cell systems. Although ras mutations are rare in human breast cancers (see (9)), ras protein overexpression has been shown to occur commonly, especially in aggressive disease, both in studies (2-5), and in other published studies (46-48).

A connection between ras/raf/MEK/ERK(MAP kinase) signaling and the induction of cyclin D1has been established in a variety of experimental systems (49-51), and is thought to occur by a mechanism that may involve ERK-mediated activation of the transcription factor ets-1 (52).

PI3 kinase is known to be a downstream effector of ras (53, 54). The inhibition of PI3 kinase by LY294002 blocks the induction of cyclin D1 and inhibits cell entry into S phase (43). Putative pathways from PI3 kinase to cyclin D1 are shown in FIG. 3. Ras-driven PI3 kinase activation is known to regulate a variety of molecular components in experimental cell systems, including PKB/Akt (43, 55) and rac (43, 55, 56). rac, in turn, has been shown to generate reactive oxygen species (56), leading to a cascade of events that results in the activation of NFkB (56). PKB/Akt can also activate NFkB (57). rac has been shown to induce cyclin D1 (43, 58-60), in cooperation with NFkB (61) and PKB/Akt (62), leading to Rb phosphorylation and E2F-dependent gene transcription (59).

Among the many different families of membrane receptors that can activate the ERK and PI3 kinase pathways both through ras-mediated and non-ras-mediated pathways, only members of the EGF receptor family are represented in FIG. 3. Even this small family of four known receptors has eight known ligands, and ten possible combinations of homo- and heterodimers, each of which could potentially activate multiple signaling pathways in addition to the ERK and PI3 kinase pathways (reviewed in (63, 64)). In actuality, the EGF receptor family heterodimers are much more potent signal transducers than the homodimers, Her-2/neu is the preferred heterodimeric partner for the other members of this receptor family (65), and Her-2/neu/erbB-3 is the most potent signal transducer among the heterodimers (66) (see (63, 64)). Membrane-associated receptor tyrosine kinases such as EGF receptor generally activate ras through various intermediary proteins (e.g., src, Shc, Grb2/Sos). erbB-3 also has docking sites for the p85 subunit of PI3 kinase in addition to an Shc binding site (67), providing for an additional pathway that bypasses ras to activate the PI3 kinase pathway directly. Heterodimerization of erbB-3, with Her-2/neu or EGF receptor has been shown to lead to increased activation of the PI3 kinase pathway in a variety of cell lines (68, 69), including breast cancer cells (70, 71), and the direct association of PI3 kinase with erbB-3 has been documented (71). This issue may prove to be pertinent to Her-2/neu-mediated, ras-independent signaling pathways that are characteristic of a specific subset of aneuploid, Her-2/neu overexpressing non-lobular breast cancers (see below).

The cyclin D1/cdk4 kinase complex is also a focal point for the actions of several inhibitors of cell cycle progression, notably p16 Ink4a, p21WAF1, and p27Kip1. The loss of p16 Ink4a in tumors with intact Rb has been noted earlier. These 'inhibitors' may play a special role in the control of progression through G1, because of their biphasic effects (72, 73). Low to moderate intracellular concentrations of p21WAF1 promote cyclin D1/cdk4 assembly and kinase activity (73, 74), whereas high intracellular concentrations of p21WAF1 inhibit cyclin D1/cdk4 kinase activity (73).

The convergence of many of these mitogenic signaling pathways on the cyclin D1/Rb pathway raises a number of interesting questions that are relevant to the development of clinical combinations of prognostic factors. For example, do Her-2/neu overexpression and ras overexpression (or, for that matter, any geno-phenotypic abnormalities that lie upstream of Rb) occur only in tumors in which Rb is intact, or are such changes also relevant in tumors in which Rb has been lost? The answer to this question is of considerable importance with regard to the grouping of optimal combinations of relevant prognostic factors for use in individual tumors. The relationship between Rb status and other relevant upstream geno-phenotypic abnormalities was studied, starting with Her-2/neu and ras. The issue of Rb status is of particular interest in lobular breast cancers. Recent findings that lobular breast cancers frequently exhibit cyclin D1 amplification/overexpression (5) would lead one to expect that Rb might be intact in such tumors.

It has been found that p53 dysfunction is present in the vast majority of non-lobular breast cancers, and that it is an early abnormality that generally precedes the development of Her-2/neu overexpression and/or ras overexpression in these tumors (4, 5). This sequence of events may arise as part of a strategy for overriding critical feedback control loops that are embedded in the intracellular signaling network of normal cells (4). These critical control loops, shown in FIG. 3, include p21WAF1-effected cell cycle blockade, primarily in G1, and pathways that lead to apoptosis when cdk inhibitor control loops are breached.

Because of its biphasic dose response effects, p21WAF1 can serve as a concentration-dependent on/off switch in an autoregulatory control loop in the cyclin D1/cdk4 kinase/Rb pathway (75-78). Early (kickstart) induction and/or post-translational stabilization of p21WAF1 is mediated by ERK (MAP kinase) (79), and occurs within 3-6 hours of mitogenic stimulation (79), in time to activate cdk4 complexed with newly induced cyclin D1. At later times (8-24 hours) after mitogenic stimulation, excessive levels of p21WAF1 can lead to inhibition of mitogenic signaling and G1 arrest (80, 81). E2F1 can induce late p21WAF1 transcription directly (76, 78). However, recent studies have shown that E2F1 and/or c-myc can also induce p19ARF (p14ARF in humans) in response to growth factor stimulation, which result in MDM2/p53 interactions that lead to p53 stabilization and p53-induced transcription of p21WAF1 (reviewed in (41)). Thus, late induction of p21WAF1 can occur by p53 mediated or by p53-independent mechanisms, particularly those involving E2F1 (76, 78), but the activation of p14ARF insures that the p53mediated pathways play an important role in this feedback loop. Other cdk inhibitors, such as p16INK4a also participate in the rasp53 autoregulatory loop (82).

FIG. 3 depicts the p21WAF1 pathway as an autoregulatory cell cycle control loop that is coupled to, but is distinct from p53-dependent apoptotic pathways (83-85). These apoptotic pathways include direct p53 transcription of bax (86), IGF-BP3 (87), and PIG-3 (88). There are other post-Rb pathways to apoptosis, however. Transactivation-deficient mutant p53 cells are still able to mount an apoptotic response (89). Also, E2F and c-myc can induce apoptosis through p53-dependent-, as well as by p53-independent mechanisms (90-93) (the latter not shown in FIG. 3).

As FIG. 3 shows, growth factor- and/or ras-mediated activation of the PI3 kinase pathway results in anti-apoptotic effects (94, 95) that can neutralize E2F- and c-myc-induced apoptotic signals (96). Specific anti-apoptotic mechanisms that have been identified include the phosphorylation and subsequent inactivation by PKB/Akt of Bad (97), a pro-apoptotic member of the Bcl2 family, and the activation of NF-kB (98) which competes directly with p53 for a limited supply of p300, a transcriptional co-activator (99, 100). The question of how and why cells choose to undergo G1 arrest or apoptosis has been studied extensively in (101)). In general, low levels of p53 activation produce G1 arrest, whereas intensive activation of p53 is more likely to lead to apoptosis (101). In terms of the model shown in FIG. 3, p53-mediated apoptosis can be viewed as a fail-safe mechanism that can be activated in the event that the p21WAF1 cell cycle regulatory loop is severely compromised.

The relative importance of p53-dependent and p53independent apoptotic mechanisms in human tumors in vivo has not been studied in detail. However, findings that p53 dysfunction is characteristic of non-lobular breast cancers and that it commonly precedes the overexpression of Her-2/neu and ras in clinical material, would suggest that wild type p53-dependent regulation of G1 cell cycle progression and/or apoptosis are, indeed, of critical importance in vivo, and that the loss of normal p53 function leaves cells especially vulnerable to a succession of intracellular signaling control system failures that can result in sustained ras-mediated mitogenic signaling.

VEGF and tumor evolutionary pathways. VEGF has been found to be a useful prognostic factor in human breast cancer (102-105). The available evidence from clinical studies suggests that VEGF overexpression may be a component of the evolutionary pathways followed by infiltrating ductal carcinomas. For example, a recent clinical breast cancer study indicates that the presence of both p53 abnormalities (a hallmark of non-lobular breast cancers) and VEGF overexpression in the same tumor conveys a worse prognosis than the presence of either or neither of these changes (106). In the few lobular breast cancers that have been studied, VEGF is either not overexpressed or is expressed at lower levels than in infiltrating ductal carcinomas (107, 108).

In experimental systems VEGF expression can be induced through receptor tyrosine kinase activation of ras (109, 110), followed by activation of the raf/MEK/ERK pathway (111-113), and/or activation of the PI3 kinase pathway (113, 114). Current studies in primary human breast cancer show that VEGF overexpression is especially common in aneuploid tumors, and is often restricted to the aneuploid tumor cell component; there is often a correlation between VEGF protein levels and ras protein levels within the same aneuploid tumor cells, but an even stronger correlation between VEGF protein levels and Her-2/neu protein levels within the same cells (see below). Based on these observations, one would assign VEGF overexpression in human breast cancer in vivo to evolutionary pathways associated with aneuploid infiltrating ductal carcinomas (see FIG. 2).

The diploid non-lobular tumor evolutionary pathway vs. the aneuploid pathway. Relatively little is known about the evolutionary pathways that lead to aggressive biological behavior in diploid infiltrating ductal carcinomas. p53 dysfunction is a hallmark of this pathway (see FIG. 2), but many of the genophenotypic abnormalities that are characteristic of aneuploid infiltrating ductal tumors occur relatively infrequently in diploid tumors. In a previous study it was found that the intracellular ratios of Her-2/neu to EGF receptor levels are low in cells from diploid infiltrating ductal carcinomas and high in aneuploid cells in infiltrating ductal carcinomas (3). It was also found that ras overexpression was more closely linked to EGF receptor overexpression than to Her-2/neu overexpression in the same cells (3) (see appendix II). Taken together, these findings suggest the possibility that EGF receptor overexpression may be closely linked with ras-mediated mitogenic signaling pathways in diploid tumor cells, while in aneuploid tumors Her-2/neu overexpression may be linked to signaling pathways that may not be as critically dependent on ras activation. EGF receptor-driven, ras-mediated signaling pathways have been well studied (see FIG. 3). The contribution of Her-2/neu-driven, ras-independent mitogenic signaling pathways to the development of tumor aggressiveness has not received close scrutiny.

Since Her-2/neu has no known ligand of its own, its activation depends almost entirely on heterodimerization with other members of the EGF receptor family (64, 115), particularly with erbB-3 (65, 70, 71). In studies of primary human breast cancers, approximately two thirds of estrogen receptor-negative tumors that overexpressed Her-2/neu also overexpressed erbB-3 (116). Since erbB-3 contains docking sites for PI3 kinase, it could provide for an additional signaling pathway that bypasses ras to activate PI3 kinase directly. Activation of PI3 kinase pathway by heregulin, a major ligand for erbB-3, has been shown to depend on the presence of other members of the EGF receptor family, particularly Her-2/neu (70, 71, 117). Thus, direct activation of the PI3 kinase pathway by Her-2/neu/c-erbB-3 heterodimers may provide a plausible mechanism for the finding of a weak linkage between Her-2/neu overexpression and ras overexpression in the same aneuploid infiltrating ductal cancer cells (3).

Intracellular clustering patterns of overexpression of EGF receptor, Her-2/neu, c-erbB-3, PI3 kinase, and ras, in primary human breast cancers are proving informative in determining which signaling pathways are relevant to the progression of diploid and aneuploid infiltrating ductal carcinomas. It is a straightforward matter to determine whether VEGF overexpression segregates with diploidy or aneuploidy in infiltrating ductal cancers (findings suggest that it occurs predominantly in aneuploid cells), how often and how strongly it is associated with ras overexpression and/or Her-2/neu in the same cells, and whether it clusters with abnormalities that are associated with the PI3 kinase pathway or with abnormalities that are associated with the ERK pathway.

Evolutionary patterns in lobular breast cancers. Much of what is known about the molecular abnormalities in lobular breast cancers has to do with the absence of many of the abnormalities that are often present in infiltrating ductal cancers. Lobular breast cancers are, for the most part, diploid, estrogen receptorpositive tumors with low S fractions. p53 abnormalities, Her-2/neu amplification/overexpression and c-myc amplification are uncommon in these tumors (4). However, lobular breast cancers do amplify and overexpress cyclin D1 (5, 122). Over 50 percent of lobular breast cancers have truncating mutations in the E-cadherin gene (27). Interestingly, both E-cadherin protein and b-catenin have been reported to be minimally expressed or absent in the vast majority of lobular breast cancers (123-126).

Cyclin D1 and E-cadherin abnormalities also occur in non-lobular breast cancers. Indeed, cyclin D1 gene amplification and protein overexpression occur commonly in infiltrating ductal cancers (127). While most non-lobular breast cancers do not have truncating E-cadherin mutations (27), reduced expression of the protein has been reported in up to 60 percent of infiltrating ductal tumors (123, 125, 126). Nevertheless, truncating E-cadherin mutations, simultaneous reduction in expression of E-cadherin and b-catenin, and cyclin D1 amplification/overexpression are among the few abnormalities that appear to occur consistently in most lobular breast cancers, and they can provide a useful point of departure for investigating the molecular abnormalities that may be characteristic of these tumors.

b-catenin links E-cadherin to the actin cytoskeleton (128, 129), and both are required to maintain cell adhesion and suppress the development of metastases (130). b-catenin also participates in the Wnt-1 signaling pathway, serving as a transcription co-factor (131, 132), which has recently been shown to upregulate cyclin D1 (44, 45).

In regard to advances in laser scanning cytometry and their impact on the design of cell-based prognostic factor studies, much of the work over the last ten years on prognostic factor analysis in primary human breast cancers has relied on the performance of multiple simultaneous fluorescence measurements on each of a large number of individual monodispersed, paraformaldehyde/methanol-fixed cells from each tumor by flow cytometry. There are advantages to the performance of measurements on intact monodispersed cells that make this approach especially appealing in the study of clinical tumor samples. Human tumor samples often consist of heterogeneous mixtures of malignant clonal cell subpopulations, normal cells (normal remnants of the tissue of origin, stromal cells, and infiltrating leukocytes), and a typical premalignant cell subpopulations that may exhibit some of the same early molecular changes that are seen in more advanced tumor components. The multiparameter cell-based studies in human breast cancer have shown that the cell subpopulations that had accumulated the largest numbers of abnormalities among those measured most often represent 5-10 percent of the cells in the sample, and, much less frequently, up to 20-25 percent. Clearly, analytical techniques that require cell disruption and the analysis of pooled cell extracts would not be optimal for the analysis of such clinical samples, due to signal averaging in heterogeneous mixtures. The technique of laser-capture microdissection was developed in order to minimize the effects of tumor heterogeneity on cell analysis in clinical material. However, the advantages of this technique are partially offset by its labor intensive nature, and by unrecognized biases in the choice and grouping of cells for study.

By comparison, the advantages of the flow cytometric approach to clinical tumor sample analysis are that 1) each cell is preserved intact for multiparameter analysis, virtually eliminating any possibility of signal averaging in heterogenous cell mixtures, 2) intracellular correlations among the measurements are preserved, 3) cell subpopulations are identified and distinguished by the type, degree, and number of measured abnormalities they contain, a process that is free of cell preselection biases, and, 4) the number of cells actually analyzed can be relatively large, typically ranging from 5,000-50,000 cells per sample. Additional advantages that distinguish flow cytometry from conventional immunohistochemical techniques include, 1) the ability to perform quantitative measurements on intact cells (in arbitrary units relative to a constant reference, or in absolute units of molecules per cell when known reference cells are included in the analysis), and, 2) the ability to minimize the effects of low-level background staining, by subtracting nonspecific background levels on a cell by cell basis (3, 4).

Disadvantages of flow cytometry have included 1) the inability to make use of correlative information relating to spatial localization and morphologic appearance of cells, and 2) progressive technical difficulties in making more than 4-5 measurements per cell routinely on clinical samples. In addition, there is extensive cell loss during the staining of cells in suspension, and many cells are excluded from the analysis electronically when measurements involve multiple laser beams. As a result, the entire clinical sample, often consisting of 1-3 million cells, must be expended to obtain four measurements on each of 5,000 to 50,000 analyzable cells. As a consequence, until this year, the pace of the multiparameter prognostic factor studies in breast cancer has been seriously hampered by the need to collect a separate cohort of clinical samples for each new four-parameter study, and by the need to follow each new patient cohort for several years before attempting to correlate patient outcomes with the measurements made on their tumors.

Laser scanning cytometry (LSC) is a relatively new technology for performing quantitative fluorescence measurements on large numbers of individual cells that have been deposited on solid media such as glass slides (133). One advantage of this technology is the ability to return to each measured cell and examine its morphology, and, in tissue sections, to return to its location within the tissue. The methodology has been worked out for performing four fluorescence measurements per cell by LSC on monodispersed cell suspensions that have been deposited on slides (135). This technology may make it possible to perform even larger numbers of measurements per cell (perhaps 6-10) in the future. However, one major benefit of this technology that has already been realized is that much higher yields of analyzable cells can be obtained in human tumor samples by LSC than by flow cytometry. 5,000-10,000 analyzable cells are obtained from tumor cell aliquots of 50,000 cells with regularity. Since paraformaldehyde/methanol-fixed cell suspensions are stable over time when stored under appropriate conditions (134), not only can they be used for the performance of prospective studies, but they can now also serve an archival function, much like formalin-fixed, paraffin-embedded tumor blocks, for the performance of "retrospective" studies on cells from the same tumor. Multiple four color panels of measurements can now be performed on aliquots of 50,000 cells each from the same tumor cell suspension, as the need for specific panels is perceived, and as such panels are developed.

In regard to correlations between patient outcome and intracellular patterns of aneuploidy, Her-2/neu overexpression and ras overexpression, early studies showed that patients whose breast cancers contained cells with Her-2/neu protein overexpression, ras protein overexpression and DNA aneuploidy in the same cells (triple positive cells), had tumor recurrence significantly more frequently than patients whose tumors contained fewer of these abnormalities, or whose tumors contained three abnormalities, but not all in the same cells (1). Originally, it was interpreted these findings in accordance with the model shown in FIG. 4, in which human solid tumor cells are thought to accumulate multiple genetic abnormalities that confer more malignant biological features on the cells that contain them, resulting in more aggressive clinical behavior (rapid and/or sustained growth‡ capacity for local invasion/acquisition of metastatic potential).

Figure 4:
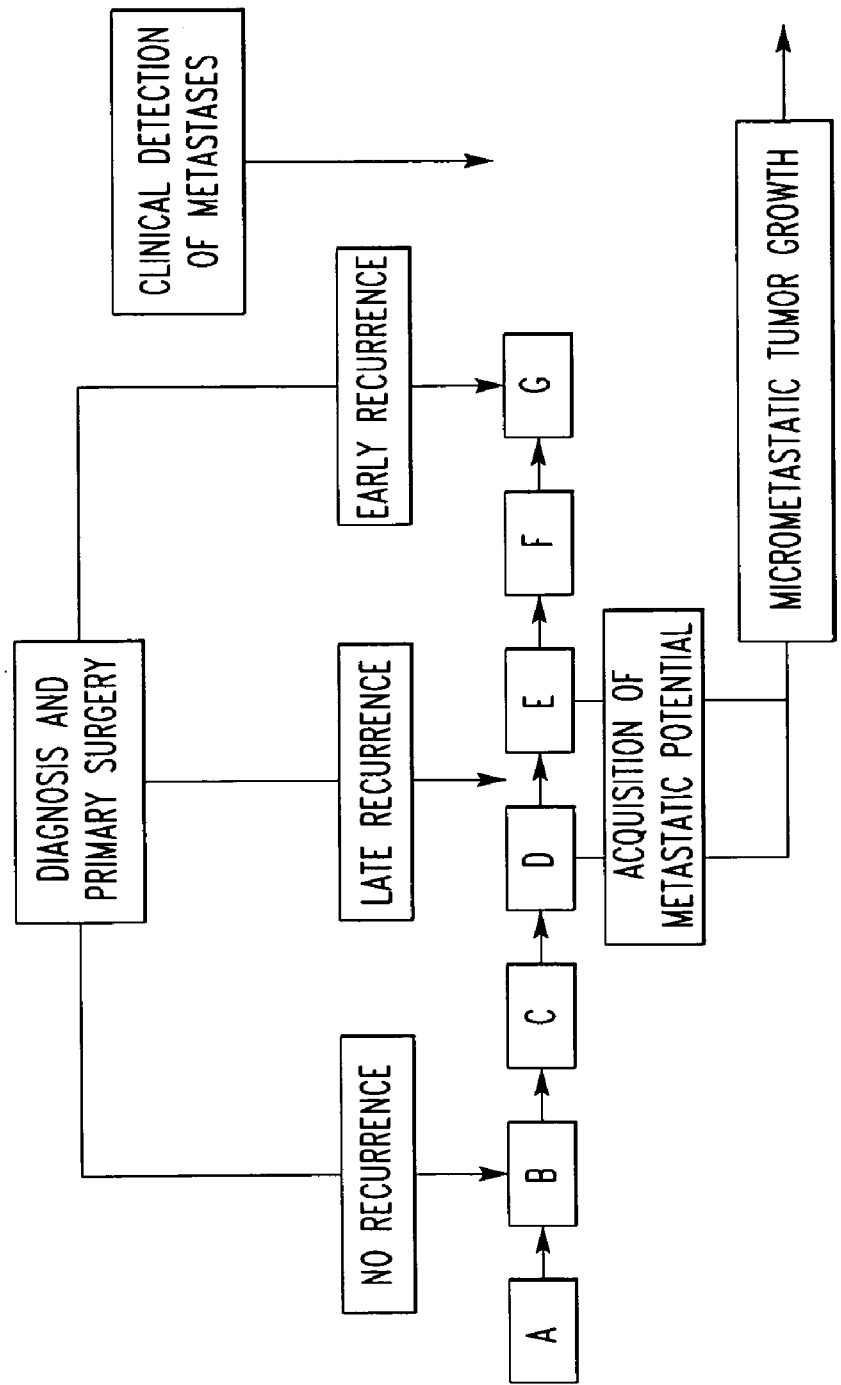
FIG. 4 shows a model relating the potential for curative surgery to the he degree of genetic evolutionary advancement of a tumor at the time of diagnosis.

FIG. 4 shows a model relating the potential for curative surgery to the he degree of genetic evolutionary advancement of a tumor at the time of diagnosis. For discussion, see text. What was of interest for prognostic purposes was a) to identifying the segment of the genetic evolutionary sequence that was associated with the acquisition of metastatic potential (abnormalities D and E in FIG. 4), and b) to determining how far a given tumor had progressed along the genetic evolutionary sequence by the time of surgery. In principle, if at the time of surgery the most advanced cells in a primary tumor had accumulated abnormalities A, and B, but not C (FIG. 4), and therefore, had not acquired the capacity to metastasize and survive at distant sites, then local treatment alone could be curative. On the other hand, if the most advanced cells in the tumor had acquired abnormalities D and E but not F or G (FIG. 4), the patient could be presumed to be at high risk for having developed metastases shortly before the time of surgery. One might anticipate that relapses in these patients would occur relatively late, since recently established small micrometastases would not be expected to become clinically apparent until cell numbers approached or exceeded 1×109 cells. In contrast, when surgery is performed at more advanced stages of primary tumor development (say, step G, FIG. 4), not only are such patients more likely to have developed micrometastatic disease, but they are likely to have developed their micrometastases long before their primary tumors were diagnosed. Such patients would have had the time to amass relatively large micrometastatic body burdens of tumor by the time of surgery; therefore, they would be at high risk for early clinical tumor recurrence.

Early clinical correlative study had indicated that the intracellular accumulation of aneuploidy, Her-2/neu overexpression and ras overexpression were components of a major evolutionary sequence in primary human breast cancers, since tumors that had produced cells containing all three of these abnormalities by the time of surgery (triple positive cells) were more likely to recur early than tumors that had not. However, based on the limited information available at the time, it was not possible to determine unambiguously where in the genetic evolutionary sequence this cluster of abnormalities belonged (e.g., at the level of C/D, D/E, or F/G in FIG. 4). The same measurements were performed on many more breast cancers under this grant, and clinical follow up has been maintained on all patients studied. A recent update of results in 190 patients, with a median time on study of 53 months (range 4-113 months) where salient findings are summarized in FIGS. 5-7.

Figure 5A:
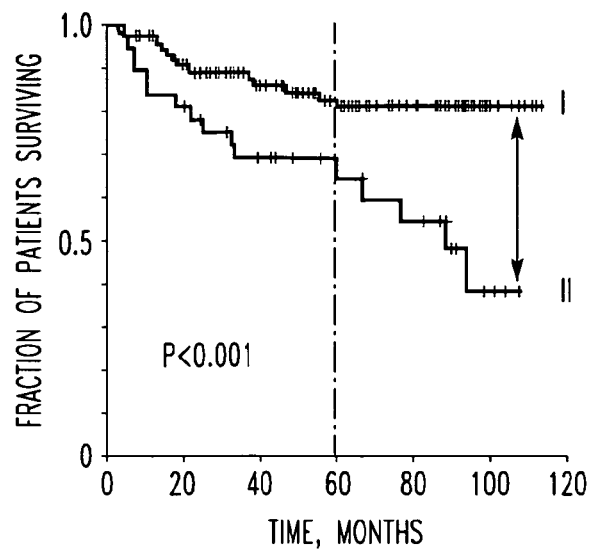
FIG. 5A shows a disease-free survival (DFS) curve for patients whose tumors contained at least 5 percent of cells that were aneuploid and also simultaneously overexpressed Her-2/neu and ras proteins (curve II), versus patients whose tumors contained less than 5 percent or no triple positive cells (curve I).
Figure 5B:
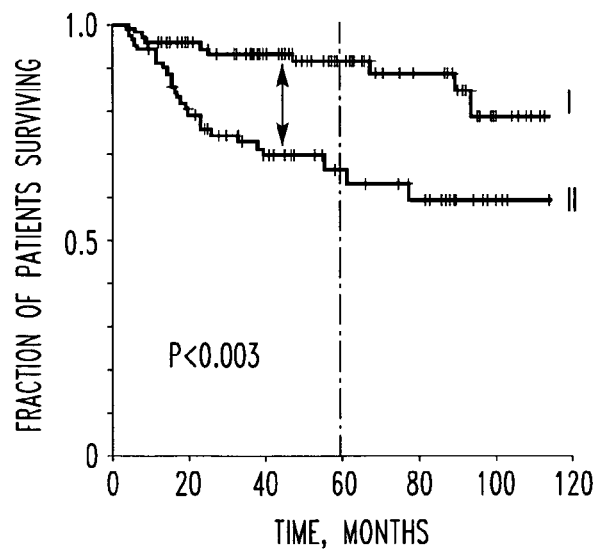
FIG. 5B shows for comparative reference, a DFS curve for patients with axillary node involvement (curve II), versus patients without axillary node involvement (curve I).

FIG. 5a shows a disease-free survival (DFS) curve for patients whose tumors contained at least 5 percent of cells that were aneuploid and also simultaneously overexpressed Her-2/neu and ras proteins (curve II), versus patients whose tumors contained less than 5 percent or no triple positive cells (curve I). A double-headed vertical arrow marks the preceding region of maximal rate of separation between the two curves, which occurs beyond five years. FIG. 5b shows for comparative reference, DFS curve for patients with axillary node involvement (curve II), versus patients without axillary node involvement (curve I). A double-headed vertical arrow marks the preceding region of maximal rate of separation between the two curves, which occurs before five years.

It is apparent from FIG. 5A that tumors containing at least 5 percent triple positive cells (curve II) recurred more frequently than tumors that did not (curve I), and that the differences were highly significant statistically. This prognostic combination was especially useful in selecting patients with late recurrences. Five patients with tumors containing triple positive cells had tumor recurrences after five years of follow up, of a total of 15 patients at risk during that interval (33 percent). In contrast, there was only one recurrence after five years among 41 patients at risk whose tumors contained fewer or no triple positive cells (2.4 percent). By comparison, the presence of tumor in axillary nodes identified patients that are at greater risk for developing early clinical recurrences, as shown by the disease-free survival curves in FIG. 5B.

Figure 6:
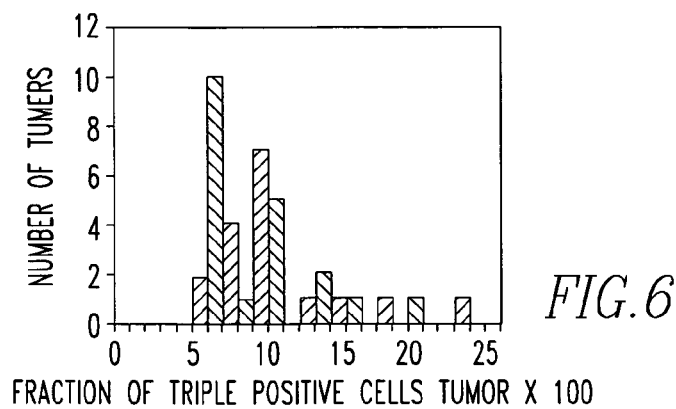
FIG. 6 shows a frequency histogram of the fractions of triple positive cells per tumor.

FIG. 6 shows a frequency histogram of the fractions of triple positive cells per tumor. In most tumors, triple positive cells represented 5-10 percent of cells present. Triple positive cells rarely represented more than 20 percent of the total, and never exceeded 25 percent of the cells in any tumor. It is of some interest that the fractions of triple positive cells in individual tumors were usually in the range of 5-10 percent, and rarely exceeded 20 percent (FIG. 6). Such small, but prognostically useful cell subpopulations might be difficult to identify, much less characterize, using non-cell-based techniques.

The lateness of many of the recurrences in patients whose tumors contained triple positive cells may have been due either to the presence of small body burdens of micrometastatic tumor at the time of surgery (see FIG. 4), to the slow growth of their micrometastases, or to both. To distinguish among these possibilities, the results of computer modeling studies were relied on that showed that patients with node negative breast cancer who recur are likely to have small micrometastases at the time of surgery, while node-positive patients who recur are likely to have relatively large subclinical tumor burdens at the time of surgery (136). The disease-free survival of patients whose tumors contained or did not contain triple positive cells separately for node-negative and node-positive patients were examined. The results, shown in FIG. 7, indicate that most of the recurrences among node-negative patients with tumors containing triple positive cells occurred at least five years after diagnosis (FIG. 7A), whereas most of the recurrences among node-positive patients with triple positive tumors occurred within the first five years of diagnosis (FIG. 7B).

Figure 7A:
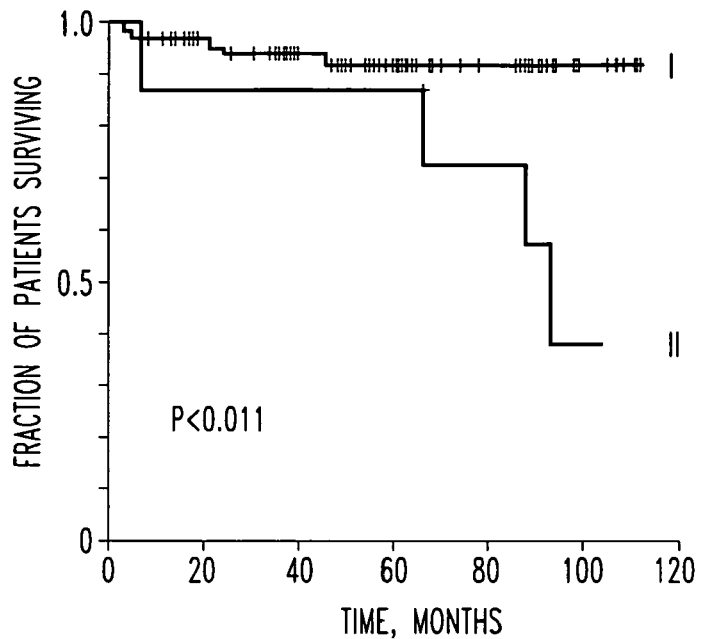
FIG. 7A shows disease-free survival of node-negative patients whose tumors contain >5 percent triple positive cells (curve II) versus DFS of node positive patients whose tumors do not contain >5 percent triple positive cells (curve I).
Figure 7B:
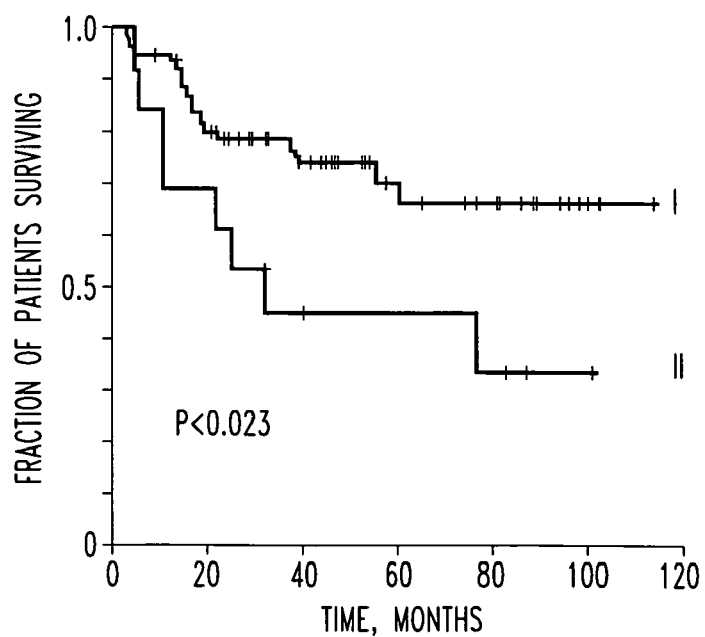
FIG. 7B shows disease-free survival of node-positive patients whose tumors contain >5 percent triple positive cells (curve II) versus DFS of node positive patients whose tumors do not contain >5 percent triple positive cells (curve I).
Figure 7C:
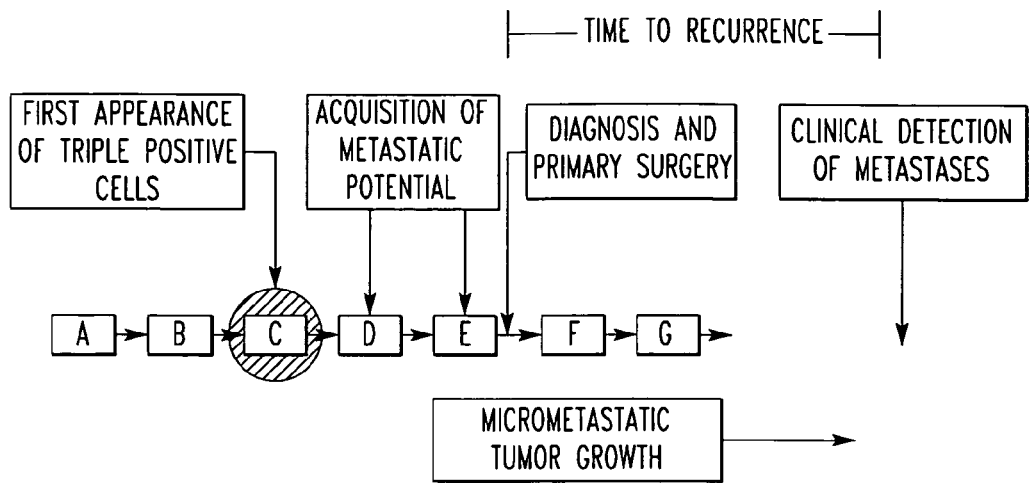
FIGS. 7C and 7D show a conceptual model to explain the relationship between the presence of triple positive cells and tumor recurrence time, and to account for the differences in the recurrence times of node-negative tumors with triple positive cells, and the recurrence times of node-positive tumors with triple positive cells.
Figure 7D:
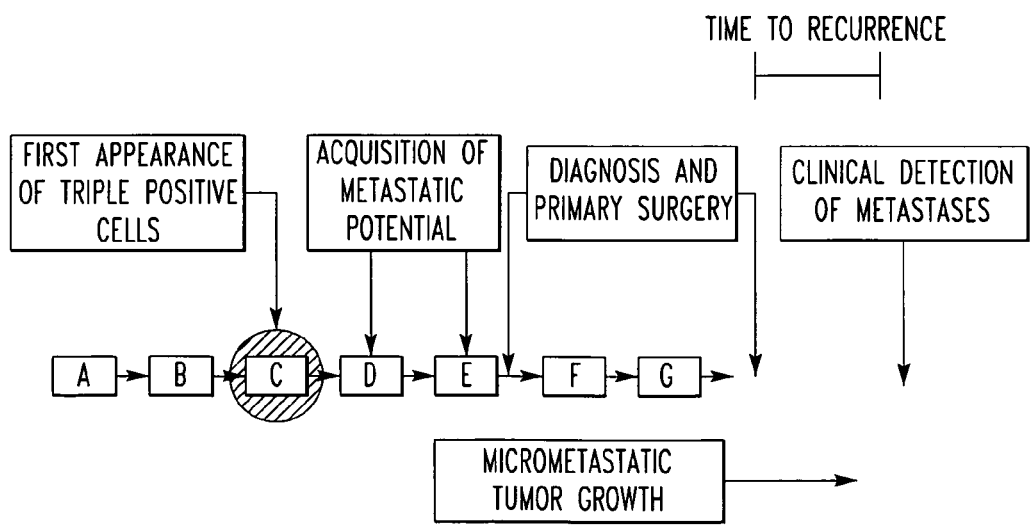

A plausible explanation for the difference between the times to recurrence of node-negative triple-positive tumors and node-positive triple positive tumors is shown schematically in FIGS. 7C and 7D. Given the long times to recurrence of node-negative tumors with triple positive cells, these tumors are likely to have been diagnosed shortly after initial micrometastatic seeding. Assuming that the presence of triple positive cells was causally related to, and, therefore, that it preceded or accompanied the acquisition of metastatic potential and the seeding of micrometastases, then the first appearance of triple positive cells could not have been a late event in the evolutionary sequence. The relatively short times to recurrence of node-positive tumors with triple positive cells would imply that the micrometastatic tumor burden was already relatively large at the time of diagnosis. Therefore, both the acquisition of metastatic potential and the earliest appearance of micrometastatic disease must have occurred long before the time of diagnosis (FIG. 7D).

FIG. 7a shows a disease free survival of node-negative patients whose tumors contain >5 percent triple positive cells (curve II) versus DFS of node positive patients whose tumors do not contain >5 percent triple positive cells (curve I). Most recurrences in tumors with triple positive cells occur at least five years beyond diagnosis. FIG. 7b shows disease-free survival of node-positive patients whose tumors contain >5 percent triple positive cells (curve II) versus DFS of node positive patients whose tumors do not contain >5 percent triple positive cells (curve I). Most recurrences in tumors with triple positive cells occur within five years of diagnosis. (FIGS. 7C and 7D) A conceptual model to explain the relationship between the presence of triple positive cells and tumor recurrence time, and to account for the differences in the recurrence times of node-negative tumors with triple positive cells (see panel A), and the recurrence times of node-positive tumors with triple positive cells (see panel B).

In regard to the identification and characterization of multiple evolutionary pathways in breast cancer, while the disease-free survival studies were maturing, efforts were devoted to elucidating the geno-phenotypic evolutionary pathways implied by the conceptual model shown in FIG. 4. It was noted that precursor cell populations often persisted in the background during later stages of tumor evolution, even in the presence of their more advanced clonal successors. Because multiple measurements were performed on each cell, one could determine how many of the measured abnormalities each clone contained, which abnormalities occurred alone in individual cells (early changes), and which abnormalities occurred only in the presence of other abnormalities that had accumulated in the same cells (late changes). This approach enabled the reconstruction of the specific sequences in which abnormalities developed in individual tumors (4).

Early studies had also identified patients whose tumors did not contain triple positive cells, but who still experienced tumor recurrences (2). The updated analysis confirmed the presence of such patients (see FIGS. 5A, 7A, and 7B). This suggested that the model depicted in FIG. 4 was highly oversimplified, in that there was not one sequence of evolutionary changes, but a choice of several evolutionary pathways that individual tumors might follow. So far, at least three branching evolutionary sequences in human breast cancer has been identified and partially characterized.

The relationships among EGF receptor, Her-2/neu, ras, and ploidy in the same cells (3) (see appendix II) were studied, and showed that, a) ras overexpression generally occurred in cells that were already overexpressing Her-2/neu, supporting the hypothesis that critical genetic abnormalities occur in a preferred sequence, and that, b) intracellular ratios of Her-2/neu and EGF receptor differed in diploid and aneuploid cells, supporting the hypothesis that diploid tumors may proceed along different genetic evolutionary pathways from aneuploid tumors. This early study also suggested that lobular breast cancers may represent a distinctive subset of diploid tumors.

In view of the close association between p53 abnormalities and the development of aneuploidy, both in clinical and in experimental studies (reviewed in (9), the intracellular correlations among p53, Her-2/neu, ras, and aneuploidy in invasive breast cancers were examined. Two recent studies, one predominantly using multiparameter flow cytometry (4), and the other based primarily on FISH data (5) indicated that lobular breast cancers were usually diploid, that they did not exhibit Her-2/neu and c-myc amplification, and that p53 abnormalities were uncommon in this histologic subtype. In contrast, the vast majority of non-lobular breast cancers (almost all of which were infiltrating ductal carcinomas), exhibited p53 dysfunction whether they were diploid or aneuploid. Non-lobular breast cancers were also distinguished from lobular tumors by the high frequency of Her-2/neu and c-myc amplification in aneuploid cells. Studies also indicated that in non-lobular tumors ras protein overexpression was a relatively late finding that almost always occurred in cells that had already developed p53 abnormalities, and particularly in aneuploid cells that had already developed p53 abnormalities and Her-2/neu overexpression (4).

A prominent role for c-myc in the development of hyper-tetraploidy (an advanced stage of aneuploidy), also emerged in FISH studies (5). In contrast, cyclin D1 amplification emerged in FISH studies as a very early abnormality that appeared in diploid cells containing no p53 abnormalities, suggesting that this was a change that could first appear prior to the bifurcation of the lobular and non-lobular genetic evolutionary pathways (5). The evolutionary pathways that have been defined so far in human breast cancers are summarized in FIG. 2.

In regard to recent multiparameter studies, there are several questions relating to the geno/phenotypic evolution of human breast cancer that are of interest for purposes of developing optimal combinations of prognostic factors: 1) VEGF as a component of the p53/aneuploid/Her-2/neu pathway that may be part of an alternative pathway to the p53->Her-2/neu-> ras pathway. 2) quantitated the absolute levels of Rb in reference cell line (molecules per cell). 3) the patterns of expression of multiple members of the EGF receptor family in the same cells in order to explore the possibility that heterodimerization of Her-2/neu with c-erbB-3 might bypass ras and activate the PI3 kinase pathway directly in p53 dysfunctional aneuploid tumor cells. 4) the possible relevance of E-cadherin and b-catenin abnormalities to mitogenic signaling through cyclin D1 in lobular breast cancers, and multicolor panels that are needed to examine the intracellular relationships among them have been developed. Findings are presented below.

For VEGF studies, multiparameter analyses on cells from 50 primary human breast cancers have been performed. The first 23 cases were analyzed by flow cytometry, and the remaining 27 cases by laser scanning cytometry. Tumor cells from the latter group have been subjected to several additional panels of measurements. To date, all have been studied with a panel consisting of cell DNA content, VEGF protein expression, Her-2/neu protein expression, and ras protein expression. Studies indicate that VEGF overexpression occurs relatively late in the course of tumor development. In most aneuploid tumors it is restricted to the aneuploid component, and is generally (but not always) found in cells that overexpress Her-2/neu. VEGF overexpression is usually found in cells that express relatively high levels of Her-2/neu. It is already apparent that VEGF will be useful in resolving steps that lie downstream of aneuploidy and/or Her-2/neu overexpression in the non-lobular breast cancer evolutionary pathways.

Figure 8:
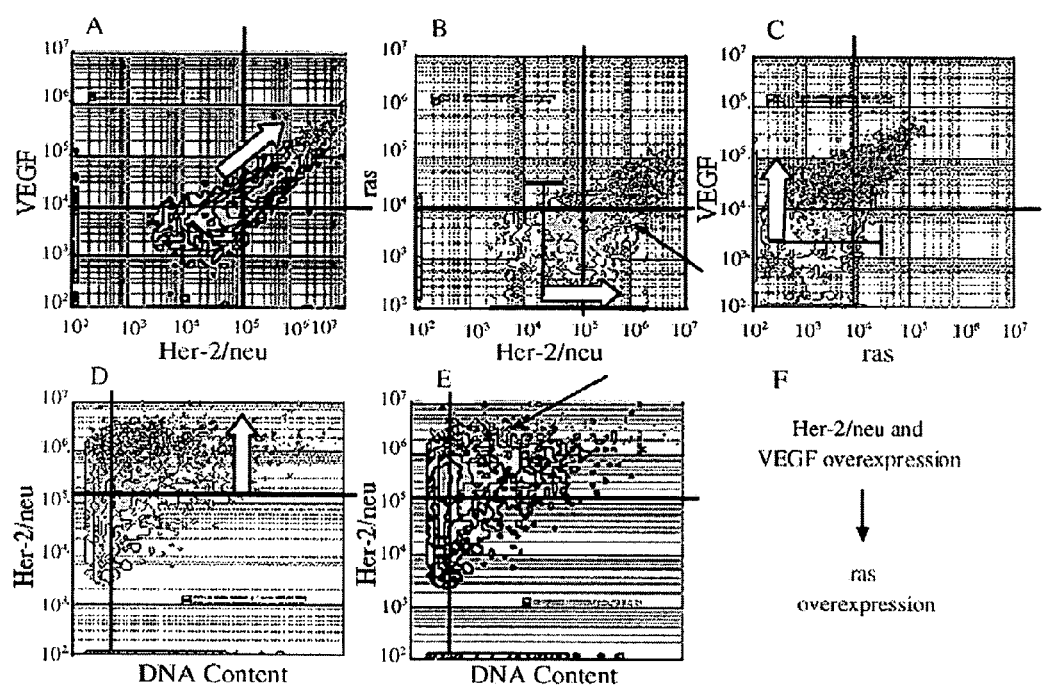
FIGS. 8A-8F show a four parameter flow cytometry study of the relationships among cell DNA content, Her-2/neu, ras, and VEGF in the same cells.

The data indicate that VEGF precedes the development of ras overexpression in many tumors. A representative example is shown in FIG. 8. In this tumor, cell DNA content, VEGF, Her-2/neu, and ras were measured in each cell by flow cytometry. The relationship between Her-2/neu expression and VEGF expression in the same cells is shown in FIG. 8A. The data are plotted as a bivariate contour map (Her-2/neu level per cell on the X axis vs. VEGF level per cell on the Y axis, and cell frequency on the perpendicular Z axis emerging toward the viewer). Cells with normal Her-2/neu levels ($<1.5 \times 10^5$ molecules per cell) and 'normal' VEGF levels (i.e., levels comparable to reference lymphocytes, or less) are found in the left lower quadrant. Cells with increased levels of both Her-2/neu and VEGF in the same cells are found in the right upper quadrant; the latter were the most abundant cells in this sample. It is apparent from FIG. 8A that there is a direct relationship between the level of Her-2/neu level per cell and the level of VEGF in the same cell. Increasing levels of Her-2/neu are accompanied by increasing levels of VEGF. It should be noted that both Her-2/neu and VEGF are plotted on a five log scale. It is apparent from FIG. 8A that the correlation between levels of Her-2/neu overexpression per cell and VEGF overexpression in the same cell holds over a hundred-fold range of overexpression of both.

FIG. 8 shows a four parameter flow cytometry study of the relationships among cell DNA content, Her-2/neu, ras, and VEGF in the same cells. Data are plotted as bivariate contour maps, with overlays of individual cells thresholded at intermediate and high levels for the third measurement (yellow and red points, respectively). Heavy vertical and horizontal lines separate regions of normal and elevated levels of Her-2/neu, ras, and VEGF, and mark the position of diploid cells on the DNA content axis.

To show the relationships among Her-2/neu, VEGF, and ras levels simultaneously, overlaid the positions of individual cells with intermediate levels of ras (>4 fold that of lymphocytes, shown in yellow), and the positions of individual cells with high levels of ras (>8 fold that of lymphocytes, shown in red) on the same graph in FIG. 8A. It is apparent that the few cells with elevated levels of ras were confined to the subset of cells that had the highest levels of both Her-2/neu and VEGF in this tumor.

The data in FIGS. 8B and 8C suggest that cells with both Her-2/neu overexpression and VEGF overexpression appeared prior to the development of cells with ras overexpression in this tumor. In FIG. 8B, Her-2/neu levels per cell are plotted against levels of ras per cell as a contour map, overlaid with the data for individual cells with intermediate VEGF levels (>5× lymphocytes in yellow) and high VEGF levels (>10× lymphocytes in red). It is apparent that among the cells that contained only one abnormality among the three cell constituents measured, almost all exhibited Her-2/neu overexpression (right lower quadrant of FIG. 8B). There were virtually no cells that contained ras overexpression alone (left upper quadrant of FIG. 8B). From this it was concluded that Her-2/neu overexpression was likely to be the first abnormality among those measured to appear in this tumor, and that the cells containing this lone abnormality persisted during later stages of tumor evolution. (Of course, it is possible that precursors with ras overexpression alone or VEGF overexpression alone had been generated early in the course of development of this tumor, but did not persist. Even so, the cells with Her-2/neu overexpression alone remain the most likely potential precursors to cells with additional abnormalities in this tumor, since these cells are the only potential precursors in evidence, and they are present in abundance).

Among the cells with Her-2/neu overexpression but no ras overexpression (right lower quadrant, FIG. 8B), there is a subset of cells with intermediate levels of VEGF overexpression (arrow, FIG. 8B), suggesting that this may have been the second abnormality to develop among those measured. This is supported by the data in FIG. 8C, in which ras levels are plotted against VEGF levels per cell, overlaid by data for individual cells overexpressing moderate levels of Her-2/neu ($>1.5 \times 10^5$ molecules per cell in yellow), and cells overexpressing high levels of Her2/neu ($>3 \times 10^5$ molecules per cell in red). Again, it is apparent that this tumor contained no cells with ras overexpression alone (right lower quadrant). There were substantial numbers of cells overexpressing VEGF but not ras in this tumor (left upper quadrant), but virtually all of them also overexpressed Her-2/neu (overlay).

FIGS. 8D and 8E show that intracellular levels of both VEGF (FIG. 8D) and ras (arrow, FIG. 8E), respectively, are correlated with Her-2/neu levels per cell independently of cell DNA content in this diploid tumor. FIG. 8F provides a reconstruction of the most likely evolutionary sequence that was followed by this tumor, based on the intracellular patterns of abnormalities found in the different cell subpopulations of this tumor.

Figure 9:
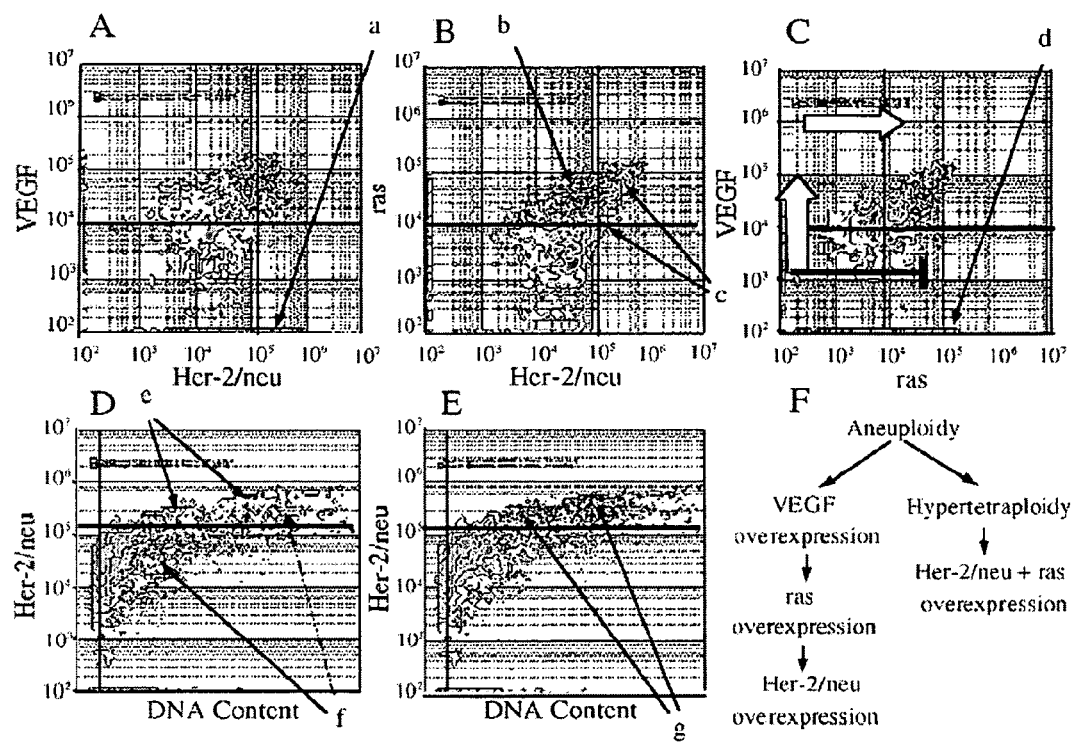
FIGS. 9A-9F show a four parameter LSC study of the relationships among cell DNA content, Her-2/neu, ras, and VEGF in the same cells.

The laser scanning cytometry data shown in FIG. 9 were obtained on cells from another human breast cancer. They reveal a more complex tumor evolutionary pattern than the previous example. The features illustrated by this example that are common to many other breast cancers are that a) VEGF overexpression is restricted to aneuploid cells, and b) VEGF overexpression precedes and occurs independently of ras overexpression. However, this case also exhibits the unusual feature of biclonality. FIG. 9D, in which the bivariate distribution of cell DNA content and Her-2/neu level per cell are plotted as a contour map, on which the positions of individual cells with moderate (yellow) and high (red) levels of VEGF overexpression are overlaid. It is apparent that VEGF overexpression occurs predominantly in an aneuploid cell subpopulation with normal to minimally elevated levels of Her-2/neu (FIG. 9D, solid arrow f). Although a few cells with high levels of VEGF are sprinkled through the hypertetraploid region (FIG. 9D, dashed arrow f), most aneuploid and hypertetraploid cells with abnormally high levels of Her-2/neu per cell (>150,000 molecules per cell) do not exhibit high levels of VEGF (FIG. 9D, arrows labeled e). In FIG. 9E the same contour map shown in FIG. 9D is overlaid with data on individual cells that overexpress intermediate (yellow) and high (red) levels of ras. It is apparent that the aneuploid and hypertetraploid cells with abnormally high levels of Her-2/neu per cell do overexpress ras, but not VEGF (compare FIG. 9D, arrows labeled e with FIG. 9E, arrows labeled g). Again, it should be noted that Her-2/neu is plotted on a five log scale in these figures, and that the different regions of VEGF and ras overexpression in FIGS. 9D and 9E, respectively, span over 50-fold differences in Her-2/neu levels per cell.

FIG. 9 shows a four parameter LSC study of the relationships among cell DNA content, Her-2/neu, ras, and VEGF in the same cells. Data are plotted as bivariate contour maps, with overlays of individual cells thresholded at intermediate and high levels for the third measurement (yellow and red points, respectively). Heavy vertical and horizontal lines separate regions of normal and elevated levels of Her-2/neu, ras, and VEGF, and mark the position of diploid cells on the DNA content axis.

The dichotomy between VEGF overexpressing and VEGF non-overexpressing cells is shown clearly in FIG. 9B, where the data on cellular levels of Her-2/neu and ras are plotted as a contour map, and the data on individual cells with increased VEGF levels are overlaid. The preponderant region of VEGF overexpression is the left upper quadrant, where cells overexpress ras, but not Her-2/neu (FIG. 9B, arrow b). In the same tumor, there is a ribbon of cells that exhibit increasing levels of both Her-2/neu and ras, but that do not overexpress VEGF (FIG. 9B, arrows labeled c).

The sequence of occurrence of VEGF and ras overexpression can be inferred from FIG. 9C. There are cells that overexpress both VEGF and ras (FIG. 9C, right upper quadrant). While the tumor contains cells with VEGF overexpression but no ras overexpression (FIG. 9C, left upper quadrant), there are virtually no cells in this tumor with ras overexpression but no VEGF overexpression (FIG. 9C, right lower quadrant). Hence, it is likely that VEGF and ras overexpressing cells were derived from the cells that overexpressed VEGF first. The cell subpopulation that overexpresses ras but is devoid of VEGF expression also shows up in this figure (FIG. 9C, arrow d). It is apparent from FIG. 9C that some of the cells with the highest levels of both VEGF and ras also overexpress Her-2/neu (FIG. 9C, overlay), implying that this occurred late.

FIG. 9A confirms the late appearance of Her-2/neu overexpression in cells that already overexpress high levels of VEGF, and that already exhibit ras overexpression (FIG. 9A, overlay). The presence of a separate cell subpopulation of cells with Her-2/neu overexpression but no VEGF is also confirmed (FIG. 9A, arrow a).

The evolutionary pathways implied by the cellular patterns of expression of Her-2/neu, VEGF and ras are summarized in FIG. 9F. Both this tumor and the tumor represented in FIG. 8 contained cell subpopulations in which VEGF overexpression first appeared prior to the overexpression of either ras, Her-2/neu, or both.

The fact that VEGF overexpression may precede Her-2/neu and/or ras in the aneuploid evolutionary sequence makes it an attractive addition to armamentarium of combined intracellular prognostic factors. Since VEGF is known to be of prognostic value in its own right, its overexpression in aneuploid, Her-2/neu-overexpressing but ras non-overexpressing cells, or in aneuploid, ras-overexpressing but Her-2/neu non-overexpressing cells could account for a substantial number of the false negative cases in FIGS. 5A and 7. Indeed, an analysis of breast cancer cases for which VEGF measurements are available shows that VEGF-overexpressing, ras non-overxpressing tumors are well represented among the recurrent tumors.

Figure 10:
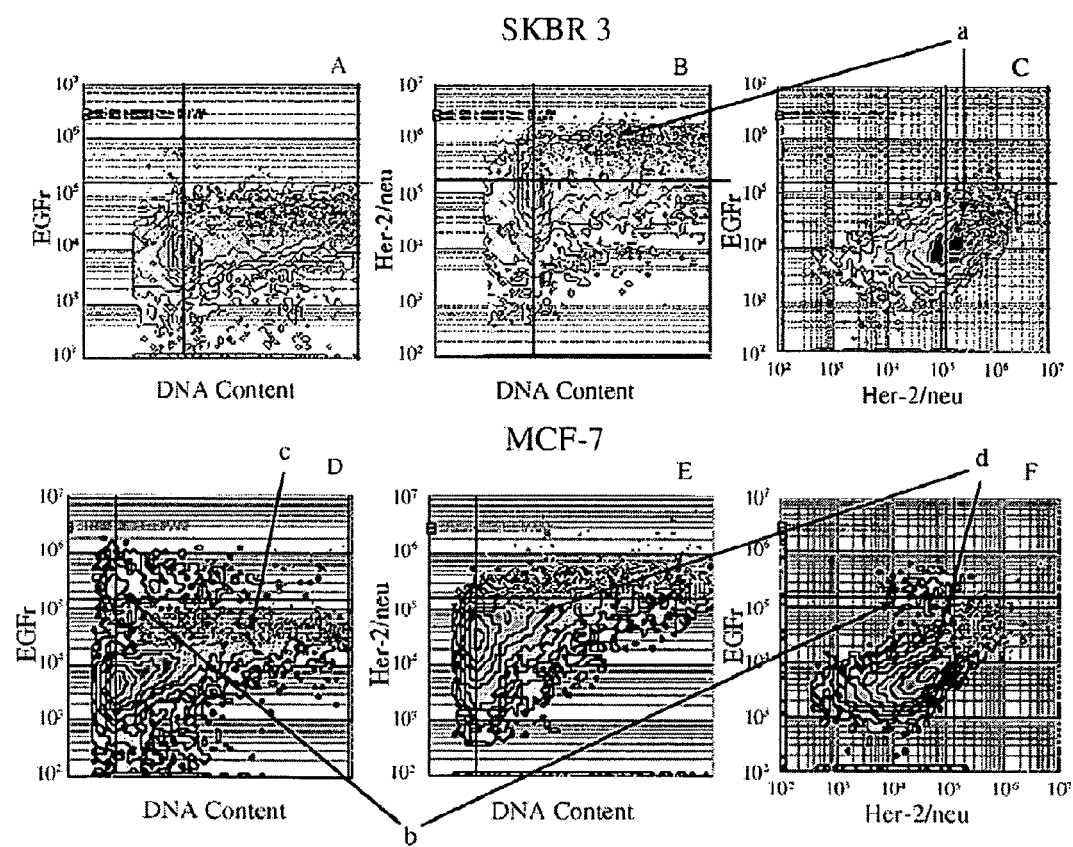
FIGS. 10A-10F show a comparison of patterns of expression of EGF receptor, Her-2/neu, and c-erbB-3 in SKBR-3 cell, and in MCF-7 cells grown in tissue culture. Data on c-erbB-3 overexpressing cells are overlaid in all panels.

Cellular patterns of receptor tyrosine kinase expression. Since it was shown previously that intracellular ratios of Her-2/neu and EGF receptor differ in diploid and aneuploid breast cancers, and since heterodimers of each of these with c-erbB-3 are much more potent mitogenic signal transducers than their respective homodimers, it was of interest to examine the levels among all three receptor tyrosine kinases in the same cells. A four color panel of correlated cellular measurements consisting of cell DNA content, and cellular levels of Her-2/neu, EGF receptor, and c-erbB-3 has been developed. Studies were performed by flow cytometry in five different established breast cancer cell lines (MCF-7, MDA-MB 231, MDA-MB 468, SKBR-3, and JC-1939. These cell lines exhibit distinctive cellular patterns of receptor tyrosine kinases. EGF receptor overexpression can occur in cells without other RTK abnormalities (MDA-MB-468 cells), while Her-2/neu overexpression is accompanied by moderate levels of expression of at least one other receptor tyrosine kinase in the same cells. The cellular patterns of receptor tyrosine kinase expression in SKBR-3 cells and MCF-7 cells are compared in FIG. 10. In SKBR-3 cells, EGF receptor levels are uniformly less than $1 \times 10^5$ molecules per cell, even in aneuploid cells, (FIG. 10A), while Her-2/neu levels exceed $1 \times 10^5$ molecules per cell in most cells, and exceed $5 \times 10^5$ molecules per cell in some (FIGS. 10B and C, arrow a). Moderately high levels of c-erbB-3 are present in the cells with the highest levels of Her-2/neu (FIGS. 10B and C, arrow a), and these cells are predominantly aneuploid (FIG. 10B, arrow a).

In contrast, MCF-7 cells contain two distinct cell subpopulations. One is a diploid population with substantial overexpression of EGF receptor alone (arrows labeled b, FIGS. 10D and 10F). The second is a subpopulation of cells with EGF receptor levels less than $1 \times 10^5$ molecules per cell (FIG. 10A), normal to minimally elevated levels of Her-2/neu per cell (arrow d, FIGS. 10E and F), and moderately increased levels of c-erbB-3 per cell, especially in the aneuploid cells with the highest Her-2/neu levels (yellow and red overlays in FIG. 10E). The maintenance of strict segregation of c-erbB-3 with cells containing aneuploid, high Her2-/neu levels (FIGS. 10B and 10E) and normal EGF receptor levels is quite striking (FIGS. 10D, arrow c, and 10F), despite the fact that these cells have been carried continuously in long-term culture. FIG. 10 shows a comparison of patterns of expression of EGF receptor, Her-2/neu, and c-erbB-3 in in SKBR-3 cell, and in MCF-7 cells grown in tissue culture. Data on c-erbB-3 overexpressing cells are overlaid in all panels.

Figure 11:
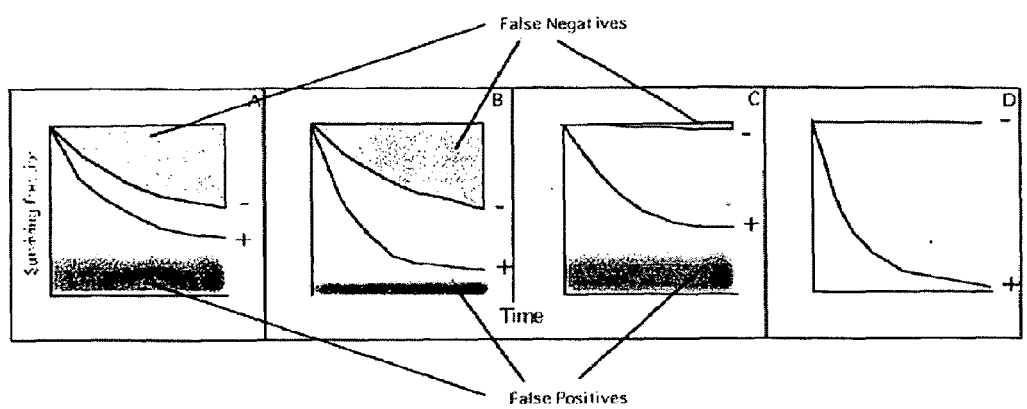
FIGS. 11A, 11B, 11C and 11D show disease-free survival curves for non-ideal (A and, B), near-ideal (C) and ideal (D) prognostic factors.

In regard to the strategy for minimizing false negatives, the purpose has been to develop reliable combinations of prognostic factors in early breast cancer that can be used to determine whether or not individual patients should receive systemic adjuvant therapy. This issue is particularly pressing in node-negative patients. According to prevailing medical opinion, systemic adjuvant therapy should be considered for the vast majority of such patients, even though 70-75 percent of them are unlikely to really need it. Because of the dire consequences of withholding potentially curative therapy from a patient with micrometastatic disease who was misclassified as being at low risk for recurrence, any combination of prognostic factors that is to be considered for use in making clinical therapeutic decisions must have an extremely low rate of false negative classification. FIG. 11 illustrates hypothetical sets of survival curves for poor (A), intermediate (B), clinically acceptable (C), and ideal (D) prognostic factor combinations. Ideally, none of patients in the favorable prognostic group would relapse no matter how long they are followed, and all of the patients in the unfavorable prognostic group would relapse if they are followed long enough (FIG. 11, panel D). For a combination of prognostic factors to be clinically acceptable, there must be very few relapses among the patients in the prognostically favorable group (FIG. 11, panel C), and there must be a spread between the cumulative recurrence rates of the favorable and unfavorable prognostic patient groups that is substantial (and, of course, statistically significant). Prognostic factors that produce small, but statistically significant differences in disease-free survival between favorable and unfavorable prognostic groups (FIG. 11, panel A), or that produce large, statistically significant spreads, but with a large proportion of prognostically favorable patients that relapse (panel B), would not be suitable for clinical use.

FIG. 11 shows disease-free survival curves for non-ideal (A and, B), near-ideal (C) and ideal (D) prognostic factors. A) A prognostic factor that produces a statistically significant difference between favorable and unfavorable groups, but which has large proportions of false negative relapsing patients and false positive non-relapsing patients of little to no value in directing clinical therapeutic decisions. B) A prognostic factor that produces a statistically significant difference between favorable and unfavorable groups, and has a low false positive rate but a high false negative rate cannot be used to assist in making clinical therapeutic decisions to withhold therapy. C) A prognostic factor that produces a statistically significant difference between favorable and unfavorable groups, and has a very low false negative rate can be used to assist in making clinical therapeutic decisions to withhold therapy, even if it has a high false positive rate. D) The ideal prognosic factor is one in which none of the members of the favorable group relapse, no matter how long they are followed, and all of the members of the unfavorable group will relapse if they are followed long enough.

In seeking to achieve better combinations of prognostic factors that would be satisfactory for use in making clinical therapeutic decisions, a focused, hypothesis-testing approach has been adopted. This approach is based on the premise that tumor cells progress along one of several evolutionary pathways, accumulating multiple geno/phenotypic abnormalities as they evolve, and eventually acquiring phenotypic attributes that enable them to metastasize. Studies to date have identified three such pathways in human breast cancer, as summarized in FIG. 2. The prognostic utility of the presence/absence of triple positive cells (aneuploidy, Her-2/neu overexpression, and ras overexpression in the same cells; FIGS. 5A and 7A and B) reflects the predominance of the p53 dysfunctional/aneuploid pathway in human breast cancer, which affects approximately 60 percent of cases. However, the false negative rate for triple positivity is still too high for this prognostic combination to be considered for clinical use at this time, even in node-negative patients (FIG. 7A).

The strategy for reducing the false negative rate further is based on the premise that tumors that did not contain triple positive cells evolved along alternative evolutionary pathways that branched off prior to the development of ras overexpression.

FIGS. 12A-E show the subclassification of the false negative breast tumors into subsets, based on intracellular patterns of ploidy and abnormalities in Her-2/neu and/or ras expression. A) Each false negative tumor belongs to one of four biologically distinctive subset of tumors (see legend) that is identified and superimposed in color-coded form on the disease free survival curves shown in FIG. 5A. B) The class of tumors that contributes the largest proportion of false negative cases consists of non-lobular cancers that contain aneuploid, Her-2/neu overexpressing, but not ras overexpressing cells. B) The class of tumors that contributes the second largest proportion of false negative cases consists of non-lobular cancers that contain aneuploid cells that overexpress neither Her-2/neu nor ras. C) Dipolid tumors contribute small proportions of flase negative cases, as do lobular breast cancers (D).

Figure 12:
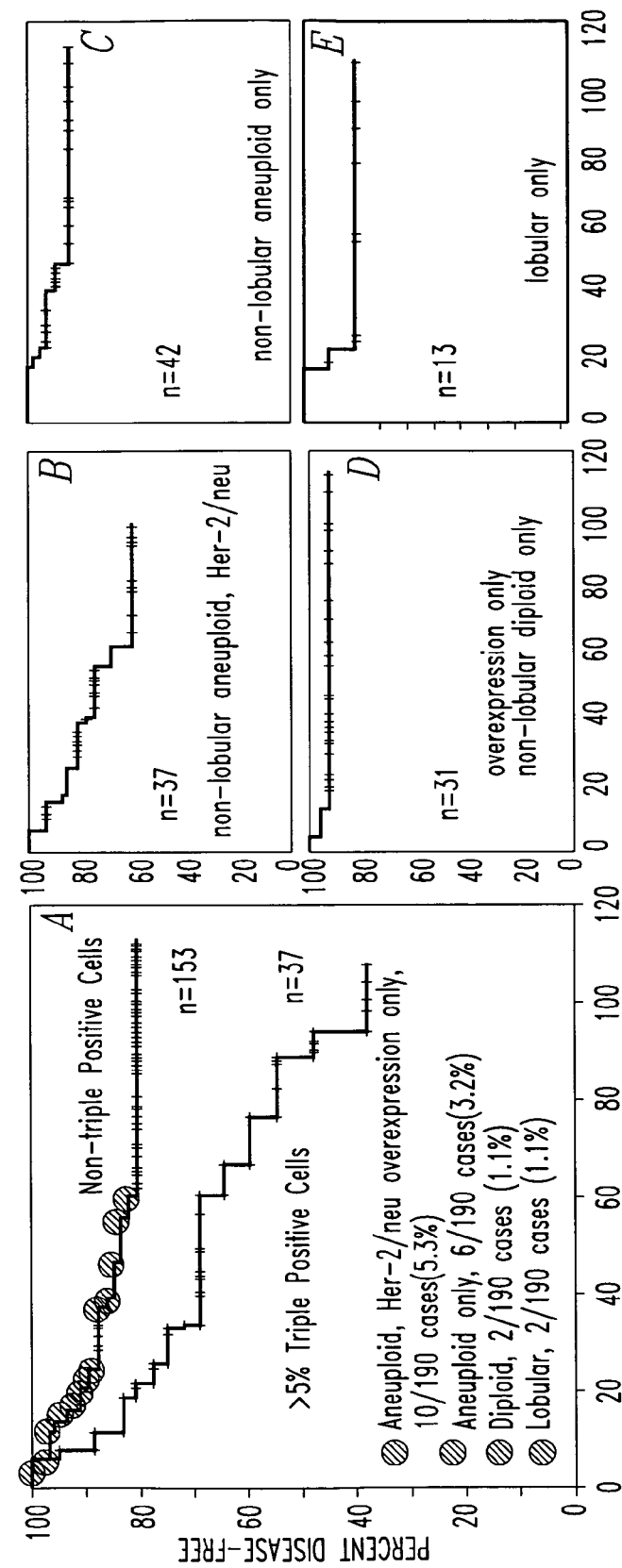
FIGS. 12A, 12B, 12C, 12D and 12E are graphs with respect to subclassification of the false negative breast tumors into subsets, based on intracellular patterns of ploidy and abnormalities in Her-2/neu and/or ras expression.

The major classes of false negative tumors are shown in FIG. 12A. Among the 20 false negative cases, 10 (50%) contained aneuploid, Her-2/neu overexpressing cells that did not overexpress ras. These were members of a subset of 37 non-lobular tumors that contained such cells, 27 of which did not recur during the course of study (FIG. 12B). The second largest group of tumors that recurred without triple positive cells (6/20 tumors, or 30%), exhibited aneuploidy, but neither Her-2/neu nor ras overexpression. These were members of a subset of 42 non-lobular tumors containing such cells, 36 of which did not recur during the course of study (FIG. 12C). The two other groups of tumors that produced recurrences despite the absence of triple positive cells are identified in FIGS. 12D and 12E as members of the subsets of non-lobular diploid tumors, and lobular tumors, respectively.

Each of the tumor subsets represented in FIGS. 12B-12D can be assigned to alternative pathways to aggressive malignancy. For example, in tumors that contain cells with aneuploidy and Her-2/neu overexpression but no ras overexpression, the presence or absence of a pathway consisting of aneuploidy->Her2-/neu overexpression->VEGF overexpression would be useful in distinguishing recurrent from nonrecurrent tumors. Similarly, in tumors that contain cells with aneuploidy but no Her-2/neu and no ras overexpression, an alternative pathway in which Rb is lost or inactivated should be useful in distinguishing recurrent tumors from nonrecurrent tumors. The major tumor subsets that produce false negatives, and the alternative evolutionary pathways most closely associated with them are summarized in FIG. 13.

FIG. 13 shows a branching evolutionary tree for human breast cancers. The triple positive pathway is shown in red. Alternative pathways that can lead to recurrences even in the absence of aneuploidy, Ger-2/beu overexpression, and ras overexpression are shown in yellow. These include the lobular pathway, several diploid pathways, an aneuploid, Her-2/neu non-overexpressing, Rb- pathway, and an aneuploid, Her-2/neu-overexpressing, VEGF-overexpressing pathway.

Relience was primarily on flow cytometry, a technology that required that each tumor sample be used in its entirety to gather four measurements per cell on each tumor. Each hypothesis-testing cycle required one to two years for tumor sample accrual and analysis, and at least three to four years of patient follow up. These methods have been adapted for use by laser scanning cytometry (135), a technology that requires only about 50,000 cells to perform a panel of four measurements per cell. Each fixed single cell suspension from a breast cancer sample that contains several million cells can serve as an archival resource for repeated sets a of maultiparameter measurements. Specific measurements to be performed on each sample include the following:

Standard single-parameter, propidium iodide-stained, DNA measurements on methanol-fixed cells by flow cytometry.

A standard four-color panel of correlated intracellular cell by cell measurements by LSC on paraformaldehyde/methanol fixed cells, consisting of cell DNA content (LDS-751), and immunofluorescence measurements of p53 protein, Her-2/neu, and ras proteins, as previously described (5).

p53 allelic loss by FISH, and amplification of Her-2/neu, cyclin D1 and c-myc by FISH on aliquots of cells fixed in methanol/glacial acetic acid (3:1) as previously described. (4).

Additional panels of four color measurements performed by LSC on separate aliqouts of cells from the same samples, that include VEGF, Rb, EGF receptor, cyclin D1, and E-cadherin.

The strategy developed here is predicated on the proven ability to perform four measurements per cell by LSC.

It should be noted that while the strategy for applying information regarding alternative evolutionary pathways is most fully developed in breast cancer, it is apparent from studies to date that is also applicable to other human solid tumors including glioblastoma, lung cancer and colon cancer. The studies are designed not to withhold unnecessary treatment from patients who are at low risk for recurrence, but to target for more aggressive therapy those patients who are at high risk for the presence of occult disease or for micromatastesis.

Data obtained in human glioblastomas and human colon cancers show that these tumors also exhibit many of the same evolutionary pathways found in breast and lung cancer, including the sequence, p53 overexpression->aneuploidy->Her-2/neu overexpression->ras overexpression. The relationships between tumors the cells of which demonstrate these sequences and clinical tumor aggressiveness can be ascertained by following these patients clinically, determining their disease-free and overall survival using standard lifetable methods, and comparing them using standard log-rank statistical techniques.

The execution of this strategy is dependent on the software developed for this purpose. The software in regard to the apparatus 10 is part of the determining means 14, which also includes a computer, and further is part of the identifying means 16, and can be stored in a memory of the computer. While many of the data display capabilities and data gating techniques that are used are also included in several commercially available programs for the general analysis of flow cytometry data, the capability to tailor the program to the specific needs herein has been critical to the ability to perform the analyses that is required. Specific unique tasks that are critical are:

The ability to specify and execute specific sequences of corrections and adjustments for each measurement, on each measured cell in the sample, e.g., clump removal, cell size-dependent correction for non-specific labeling in the linear domain for log data).

The ability to perform multicolored and multiple thresholded overlays (unique to the computer program herein).

The ability to read multiparameter cell-based data obtained by laser scanning cytometry in ASCII format (unique to the computer program herein).

The ability to continuously update the program to adapt to changing computer capabilities, and to meet the evolving needs.

A computer program description in regard to its general features and organization is now provided.

The program is written in c for the Macintosh, and is designed around a typical event-driven infinite loop, with a typical Macintosh look-and-feel window-based graphical user interface. Menu items include a) File: file-related functions, b) Presentation: functions that deal with data display and preprocessing prior to analysis, c) Analysis: data analysis functions and, d) Report: facilities for organization, display and storage of processed data. e) File:

Get list mode file: User specifies a list mode file containing flow cytometry data that were collected in standard FCS format (ref), which are read into an array in memory, where the rows represent the data for individual tumor cells, and the columns represent the different measurements performed on each cell. Data are binned into histograms consisting of 256 channels. Reference values and scale factors for each measurement type are entered separately by the user (see below).

Save ASCII data file: The list mode array can be saved on disk in ASCII format after preprocessing, together with user-generated instructions for subsequent analysis.

Read ASCII data file: A list mode array previously saved on disk in ASCII format after preprocessing together with user-generated instructions for subsequent analysis can be read into memory.

Read reference data file: An ASCII file containing reference values and scale factors for each measurement (prepared separately in another program) can be read into memory for use in data analysis.

In Regard to Presentation:

Single parameter: Any of the measurements made on individual cells (columns in the data array) can be displayed as single parameter frequency histogram with 256 classes. Cell DNA content is always one of those measurements. The first step in the standard procedure for data preprocessing includes removing cells in the highest channel in the histogram from the data array; these data represent cell clumps. The DNA histogram invariably includes a peak of cells with the lowest bona fide DNA content levels (the G1 peak). "Cells" with DNA contents that fall below this peak are actually cell fragments, and are also removed from the data array list during preprocessing.

Two parameters: Pairs of measurement types (two columns from the data array) chosen by the user are used to construct a bivariate frequency histogram, which is displayed on a 64×64 grid. This can be displayed as a dot plot, a 2D projection of the 3D histogram (channel numbers of parameters A and B on the X and Y axes respectively, and their joint frequencies on the Z axis), or as a contour map. The contour map is routinely used.

Data Preparation: This screen that allows the user to set down a series of specific instructions to be carried out in a specific order on each cell measurement in order to prepare the data for subsequent analysis. The first instruction for each non-DNA measurement specifies the level of nonspecific labeling to be subtracted from each cell based on reference values that are either entered by the user or read in under menu item File>Read reference data (see above). The second instruction specifies a numerical value that is assigned to an appropriate reference channel to calibrate the data (as multiples of some arbitrary reference value, or in absolute molecules/per cell). The numerical values and reference channels for each measurement are entered by the user or read in under menu item File>Read reference data. Finally, scaling factors are specified for the graphical representation of each measurement. On the linear scale, the maximum displayed value is assigned to channel 255. On a log scale, the lowest displayed value is assigned to channel 0, and the number of log cycles to be displayed is specified. The instructions are then all applied sequentially on command by the user, and the processed data are then plotted as scaled contour maps ready for analysis.

In regard to use of the computer program to identify patients at high risk for tumor recurrence, it has previously been shown (The Cancer Journal, 2: 105-114,1996) that tumors in which at least 5 percent of cells that exhibit aneuploidy, Her-2/neu overexpression and ras overexpression in the same cells, are more likely to recur than tumors in which less than 5 percent of cells contain all three abnormalities. The computer program developed for the analysis of multiparameter flow cytometry or laser scanning cytometry data is required to determine the fraction of cells that contain all three abnormalities in each tumor, and identify the patients who are at high risk for recurrence.

The Procedure is as Follows:
1. Samples obtained from human tumors are mechanically disaggragated by scissor mincing in order to obtain single cell suspensions. The cells are fixed in paraformaldehyde and methanol, as previously described (The Cancer Journal, 2: 105-114,1996), stained for cell DNA content, Her-2/neu and ras, and analyzed by flow cytometry as previously described (The Cancer Journal, 2: 105-114,1996). Each tumor data set consists of an array of cell by cell measurements (rows), where the columns consist of individual measurements performed on each cell—cell DNA content, Her-2/neu, and ras. These arrays are stored in standard FCS format by the flow cytometry instrument. Typically, 10,000-50,000 cells are analyzed in each tumor.
2. The data array for each tumor is read into memory by the computer program, and prepared for analysis as follows:
    A 256-bin histogram is generated for each measurement. Data associated with cell clumps are removed (by zeroing out cells that contribute to channel 255 of the DNA histogram), and data associated with cell fragments are removed (by zeroing out cells that contribute to channels that lie below the G1 peak of the DNA histogram, [usually channels 0-30 or higher, depending on the position of the G1 peak in any given sample, as determined by visual inspection of the DNA histogram]). Typically, when data generated by clumps and cell debris are removed from a sample containing 30,000 cell events, data for approximately 20,000 intact single cells remain. This clump and fragment removal process is accomplished through a graphical user interface with menu options for selecting the histogram to be graphed, and for identifying and selecting the channel ranges to be included or excluded from the analysis.

Reference data are read into memory to provide for relating channelized data values to relative or absolute real-world quantities. Cell DNA content measurements are always collected in the linear domain rather than the log domain, and are always referenced internally by the position of the G1 peak in each sample. Her-2/neu data are collected in the log domain, and are referenced to concomitantly measured external cell line of known Her-2/neu content per cell. Thus, for example, if the mean channel value for the concomitantly run reference cell line is channel 63, and the reference cell line is known to have a mean of 50,000 molecules of Her-2/neu per cell, then all cells in the tumor cell sample that fall in channel 63 are assigned a value of 50,000 molecules per cell. Since log data are generally collected over a four decade range that is mapped onto 256 channels, then with each 64 channel increment, the Her-2/neu value assignment increases by a factor of 10. For example, if cells appearing in channel 63 are assigned a reference value of 50,000 molecules of Her-2/neu per cell, then cells appearing in channel 127 will be assigned a Her-2/neu value that is 10-fold higher, or 500,000 molecules per cell. When the absolute levels of the quantity measured in the reference cells is not known, the tumor cell measurements are expressed in relative units with regard to the reference cells. Thus, for the ras measurement, normal lymphocytes are assigned an arbitrary value of 10,000 units per cell, and set in an arbitrarily low reference channel. Thus, for example, if the lymphocyte reference is set in channel 63, tumor cells that fall in the same channel are assigned a value of 10,000 arbitrary units of ras per cell, and tumor cells that fall in channel 127 will be assigned a value of 100,000 arbitrary units per cell.

Data can be rescaled for graphing purposes, depending on the range of observed measurements. Since the range of some measurements can span >1,0000-fold, but rarely exceeds 10,000-fold, all log measurements are scaled on a 5-cycle log scale.

When three or more measurements are performed on each cell, one can conveniently display the inter-relationships among any two as bivariate frequency histogram, where the amount of measured substance A is plotted on the X axis, the amount of measured substance B is plotted on the Y axis, and the frequency of cells with different levels of both A and B on the Z axis (projected as a contour map). The overlay technique consists of performing thresholding operations on measurement C at one or more levels (say intermediate and high levels of C) and overlaying plots of threshold-dependent color-coded dots representing the X and Y values of cells that have levels of C above the designated thresholds. Thus, for example, if all cells that have high levels of C also have high levels of A and B, the color-coded dots will show up in the right upper quadrant of the bivariate histogram.

The data are then plotted as bivariate frequency histograms in the form of contour maps on a 64×64 box grid. The DNA histogram generally exhibits two peaks—the lower peak is the G1 peak and is usually centered between channels 40 and 60 of a 256 channel histogram. The higher peak is the G2 peak, which is usually centered at about twice the mean value of the G1 peak, commonly between channels 80 and 120. The region of interest in a cell DNA vs. Her-2/neu plot lies beyond the G2 region on the DNA axis and above the channel that corresponds to 150,000 molecules per cell on the Her-2/neu axis. All individual cells with DNA contents that have DNA contents above this range are aneuploid. The computer program, through a menu driven interface, allows the user to create user-defined rectangular regions that overlie the bivariate contour map. Individual cells that fall within the ranges of values defined by these rectangular regions can then be included or excluded from a newly generated separate data array. This is called data gating. Thus, for example, if one defines a rectangular region that includes all values above channel 120 on the DNA axis and above the channel that corresponds to 150,000 Her-2/neu molecules per cell, and includes only those cells that fall within these gates in a newly generated data array, then one would isolate a subpopulation of cells each of which is both aneuploid and a Her-2/neu overexpressor. Since the ras data associated with these cells is preserved in the new array, one can then generate a bivariate contour map that includes ras along one of the axes (say Her-2/neu vs. ras), and perform a second data gating operation that retains only those cells that have levels of ras overexpression that are at least 4-fold higher than the mean value for normal lymphocytes. Not only are the cells that are retained after this second gating procedure aneuploid and Her-2/neu overexpressors, but they are ras overexpressors as well. Since the number of intact single cells in the entire sample is known, and the number of cells that meet the criteria for three abnormalities per cell is known, the program can calculate the fraction of the tumor cells that are triple positive. Studies have shown that if this triple positive cell fraction exceeds 5 percent in a given tumor, that patient is at high risk for recurrence.

The same procedure can be applied to additional aliquots of cells from the same tumor that have been stained with other fluorescent probes.

Generally, high risk of reoccurrence of cancer means a 5% or greater chance of reoccurrence of the cancer. Preferably, the 5% or greater chance of reoccurrence of cancer is for breast cancer.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

Literature Cited, all of which is incorporated by reference herein.

1. Braun, S., Pantel, K., Muller, P., Janni, W., Hepp, F., Kentenich, R., Gastroph, S., Wischnik, A., Dimpfl, T., Kindermann, G., Riethmuller, G., and Schlimok, G. Cytokeratin-positive cells in the bone marrow and survival of patients with stage I, II, or III breast cancer, The New England Journal of Medicine. 342: 525-533, 2000.
2. Shackney, S., Pollice, A., Smith, C., Alston, L., Singh, S., Janocko, L., Brown, K., Petruolo, S., Groft, D., Yakulis, R., and Hartsock, R. The accumulation of multiple genetic abnormalities in individual tumor cells in human breast cancers: Clinical prognostic implications, The Cancer Journal. 2: 105-114, 1996.
3. Shackney, S., Pollice, A., Smith, C., Janocko, L., Sweeney, L., Brown, K., Singh, S., Gu, L., Yakulis, R., and Lucke, J. Intracellular coexpression of epidermal growth factor receptor, Her-2/neu, and p21 ras in human breast cancers: Evidence for the existence of distinctive patterns of genetic evolution that are common to tumors from different patients, Clinical Cancer Research. 4: 913-928, 1998.
4. Smith, C., Pollice, A., Gu, L. -P., Brown, K., Singh, S., Janocko, L., Johnson, R., Julian, T., Hyams, D., Wolmark, N., Sweeney, L., Silverman, J., and Shackney, S. Correlations Among p53, Her-2/neu, and ras Overexpression and Aneuploidy by Multiparameter Flow Cytometry in Human Breast Cancer: Evidence for a Common Phenotypic Evolutionary Pattern in Infiltrating Ductal Carcinomas, Clinical Cancer Research. 6: 112-126, 2000.
5. Janocko, L., Brown, K., Smith, C., Gu, L., Pollice, A., Singh, S., Julian, T., Wolmark, N., Sweeney, L., Silverman, J., and Shackney, S. Distinctive patterns of Her-2/neu, c-myc, and cyclin D1 gene amplification by fluorescence in situ hybridization (FISH) in primary human breast cancers, submitted for publication, 2000.
6. Jares, P., Rey, M., Fernandez, P., Campo, E., Nadal, A., Munoz, M., Mallofre, C., Muntane, J., Nayach, I., Estape, J., and Cardesa, A. Cyclin D1 and retinoblastoma gene expression in human breast carcinoma: Correlation with tumour proliferation and oestrogen receptor status, Journal of Pathology. 182: 160-166, 1997.
7. Tsuda, H., Fukutomi, T., and Hirohashi, S. Pattern of gene alterations in intraductal breast neoplasms associated with histological type and grade, Clinical Cancer Research. 1: 261-267, 1995.
8. Courjal, F., M, C., Simony-Lafontaine, J., Louason, G., Speiser, P., Zeillinger, R., Rodriguez, C., and Theillet, C. Mapping of DNA Amplifications at chromosomal localizations in 1875 breast tumors: definition of phenotypic groups, Cancer Research. 57: 4360-4367, 1997.

9. Shackney, S. and Shankey, T. Common patterns of genetic evolution in human solid tumors, Cytometry. 29: 1-27, 1997.
10. Hovey, R., Chu, L., Balasz, M., DeVries, S., Moore, D., Sauter, G., Carrol, P., and Waldman, F. Genetic alterations in primary bladder cancers and their metastases, Cancer Research. 58: 3555-3560, 1998.
11. Hellman, R., Lan, F., McBride, R., and Hellman, S. Separating favorable from unfavorable prognostic markers in breast cancer: the role of E-cadherin, Cancer Research. 60: 298-304, 2000.
12. Lengauer, C., Kinzler, K., and Vogelstein, B. Genetic instability in colorectal cancers, Nature. 386: 623-627, 1997.
13. Fearon, E. and Vogelstein, A. A Genetic model for colorectal tumorigenesis, Cell. 61: 759-767, 1990.
14. Allred, D., O'Connell, P., Fuqua, S., and Osborne, C. Immunohistochemical studies of early breast cancer evolution, Breast Cancer Research and Treatment. 32: 13-18, 1994.
15. Ried, T., Heselmeyer-Haddad, K., Blegen, H., Schrock, E., and Auer, G. Genomic changes defining the genesis, progression, and malignancy potential in solid human tumors: a phenotype/genotype correlation, Genes, Chromosomes & Cancer. 25: 195-204, 1999.
16. Galipeau, P., Cowan, D., Sanchez, C., Barrett, M., Emond, M., Levine, D., Rabinovitch, P., and Reid, B. 17P (p53) allelic losses, 4N (G2/tetraploid) populations and progression to aneuploidy in Barrett's esophagus, Proc.Nat.Acad. Sci. USA. 93: 7081-7084, 1996.
17. Blount, P., Galipeau, P., Sanchez, C., Neshat, K., Levine, D., Yin, J., Suzuki, H., Abraham, J., Meltzer, S., and Reid, B. 17p allelic losses in diploid cells of patients with Barrett's esophagus who develop aneuploidy, Cancer Research. 54: 2292-2295, 1994.
18. Neshat, K., Sanchez, C., Galipeau, P., Blount, P., Levine, D., Joslyn, G., and Reid, B. p53 mutations in Barrett's adenocarcinoma and high grade dysplasia, Gastroenterology. 106: 1589-1595, 1994.
19. Barrett, M., Sanchez, C., Prevo, L., Wong, D., Galipeau, P., Paulson, T., Rabinovitch, P., and Reid, B. Evolution of neoplastic cell lineages in Barrett Oesophagus, Nature Genetics. 22: 106-109, 1999.
20. Carder, P., Wyllie, A., Purdie, C., Morris, R., White, S., Piris, J., and Bird, C. Stabilized p53 facilitates aneuploid clonal divergence in colorectal cancer, Oncogene. 8: 1397-1401, 1993.
21. Carder, P., Cripps, K., Morris, R., Collins, S., White, S., Bird, C., and Wyllie, A. Mutation of the p53 gene precedes aneuploid clonal divergence in colorectal carcinoma, Br. J. Cancer. 71: 215-218, 1995.
22. O'Malley, F., Vnencak-Jones, C., Dupont, W., Parl, F., Manning, S., and Page, D. p53 mutations are confined to the comedo type ductal carcinoma In Situ of the breast (Immunohistochemical and Sequencing Data), Laboratory Investigation. 71: 67-72, 1994.
23. Horsfall, D., Tilley, W., Orell, S., Marshall, V., and Cant, E. M. Relationship between ploidy and steroid hormone receptors in primary invasive breast cancer, Br. J. Cancer. 53: 23-28, 1986.
24. Escot, C., Theillet, C., Lideeau, R., Spyratos, F., Champeme, M. -H., Gest, J., and Callahan, R. Genetic alterations of the c-myc protooncogene (MYC) in human primary breast carcinomas, Proc. Natl. Acad. Sci USA. 83: 4834-4838, 1986.
25. Varley, J., Brammar, W., and Walker, R. Oncogene organization and expression: Prediction in breast cancer, Horm Res. 32 (suppl 1): 250-253, 1989.
26. Domagala, W., Markiewski, M., Kubiak, R., Bartkowiak, J., and Osborn, M. Immunohistochemical profile of invasive lobular carcinoma of the breast: Predominantly vimentin and p53 protein negative, cathepsin D and oestrogen receptor positive, Virchows Archiv A Pathological Anatomy and Histopathology. 423: 497-502, 1993.
27. Berx, G., Cleton-Jansen, A. -M., Strumane, K., de Leeuw, W., Nollet, F., van Roy, F., and Cornelisse, C. E-cadherin is inactivated in a majority of invasive lobular breast cancers by truncation mutations throughout its extracellular domain, Oncogene. 13: 1919-1925, 1996.
28. Moll, R., Mitze, M., Frixen, U., and Birchmeier, W. Differential loss of E-cadherin expression in infiltrating ductal and lobular breast carcinomas, American Journal of Pathology. 143: 1731-1742, 1993.
29. Siitonen, S., Kononen, J., Helin, H., Rantala, I., Holli, K., and Isola, J. Reduced E-cadherin expression is associated with invasiveness and unfavorable prognosis in breast cancer, American Journal of Clinical Pathology. 105: 394-402, 1996.
30. Jones, J., Royall, J., and Walker, R. E-cadherin relates to EGFR expression and lymph node metastasis in primary breast carcinoma, British Journal of Cancer. 74: 1237-1241, 1996.
31. Bartkova, J., Lukas, J., Muller, H., Lutzhoft, D., Strauss, M., and Bartek, J. Cyclin D1 protein expression and function in human breast cancer, Int. J. Cancer. 57: 353-361, 1994.
32. Okamoto, A., Demetrick, D., Spillare, E., Hagiwara, K., Hussain, S., Bennett, W., Forrester, K., Gerwin, B., Serrano, M., Beach, D., and Harris, C. Mutations and altered expression of p16INK4 in human cancer, Proc. Natl. Acad. Sci. USA. 91: 11045-11049, 1994.
33. Bates, S., Parry, D., Bonetta, L., Vousden, K., Dickson, C., and Peters, G. Absence of cyclin D/cdk complexes in cells lacking functional retinoblastoma protein, Oncogene. 9: 1633-1640, 1994.
34. Lukas, J., Parry, D., Aagaard, L., Mann, D., Bartkova, J., Strauss, M., Peters, G., and Bartek, J. Retinoblastoma-protein-dependent cell-cycle inhibition by the tumour suppressor p16, Nature. 375: 503-506, 1995.
35. Parry, D., Bates, S., Mann, D., and Peters, G. Lack of cyclin D-Cdk complexes in Rb-negative cells correlates with high levels of p16INK4/MTS1 tumour suppressor gene product, The EMBO Journal. 14: 503-511, 1995.
36. Aagaard, L., Lukas, J., Bartkova, J., Kierulff, A. -A., Strauss, M., and Bartek, J. Aberrations of p16Ink4 and retinoblastoma tumour-suppressor genes occur in distinct sub-sets of human cancer cell lines, Int. J. Cancer. 61: 115-120, 1995.
37. Nielsen, N., Emdin, S., Cajander, J., and Landberg, G. Deregulation of cyclin E and D1in breast cancer is associated with inactivation of he retinoblastoma protein, Oncogene. 14: 295-304, 1997.
38. Lukas, J., Muller, H., Bartkova, J., Spitkovsky, D., Kjerulff, A., Jansen-Durr, P., Strauss, M., and Bartek, J. DNA tumor virus oncoproteins and retinoblastoma gene mutations share the ability to relieve the cell's requirement for cyclin D1function in G1, J.Cell Biol. 125: 625-638, 1994.
39. Weinberg, R. The retinoblastoma protein and cell cycle control, Cell. 81: 323-330, 1995.
40. Nevins, J. Toward an understanding of the functional complexity of the E2F and retinoblastoma families, Cell Growth & Differentiation. 9: 585-593, 1998.

41. Sherr, C. Tumor Surveillance via the ARF-p53 pathway, Genes & Development. 12: 2984-2991, 1998.
42. Lukas, J., Bartkova, J., and Bartek, J. Convergence of mitogenic signalling cascades from diverse classes of receptors at the cyclin D-cyclin-dependent kinase-pRb-controlled G1 checkpoint, Molecular and Cellular Biology. 16: 6917-6925, 1996.
43. Gille, H. and Downward, J. Multiple ras effector pathways contribute to G1 cell cycle progression, The Journal of Biological Chemistry. 274: 22033-22040, 1999.
44. Tetsu, O. and McCormick, F. b-Catenin regulates expression of cyclin D1in colon carcinoma cells, Nature. 398: 422-426, 1999.
45. Shtutman, M., Zhurinsky, J., Simcha, I., Albanese, C., D'Amico, M., Pestell, R., and Ben-Ze'ev, A. The cyclin D1gene is a target for the b-catenin/LEF-1 pathway, Proceedings of the National Academy of Sciences USA. 96: 5522-5527, 1999.
46. Lundy, J., Grimson, R., Mishriki, Y., Chao, S., Oravez, S., Fromowitz, F., and Viola, M. Elevated ras oncogene expression correlates with lymph node metastases in breast cancer patients, Journal of Clinical Oncology. 4: 1321-1325, 1986.
47. Clair, T., Miller, W., and Cho-Chung, Y. Prognostic significance of the expression of a ras protein with a molecular weight of 21,000 by human breast cancer, Cancer Research. 47: 5290-5293, 1987.
48. Dati, C., Muraca, R., Tazartes, O., Antoniotti, S., Perroteau, I., Giai, M., Cortese, P., Sismondi, P., Saglio, G., and DeBortoli, M. c-erbB-2 and ras expression levels in breast cancer are correlated and show a co-operative association with unfavorable clinical outcome, In. J. Cancer. 47: 833-838, 1991.
49. Liu, J. -J., Chao, J. -R., Jiang, M. -C., N. O., S. -Y., Jong-Young Yen, J., and Yang-Yen, H. -F. Ras transformation results in an elevated level of cyclin D1and acceleration of G1 progression in NIH 3T3 cells, Molecular and Cellular Biology. 15: 3654-3663, 1995.
50. Winston, J., Coats, S., Wang, Y. -Z., and Pledger, W. Regulation of the cell cycle machinery by oncogenic ras, Oncogene. 12: 127-134, 1996.
51. Aktas, H., Cai, H., and Cooper, G. Ras links growth factor signaling to the cell cycle machinery via regulation of cyclin D1and the cdk inhibitor p27Kip1, 17: 3850-3857, 1997.
52. Kerkhoff, E. and Rapp, U. Cell cycle targets of Ras/Raf signalling, Oncogene. 17: 1457-1462, 1998.
53. Rodriguez-Viciana, P., Warne, P., Vanhaesebroeck, B., Waterfield, M., and Downward, J. Activation of phosphatidylinositol 3-kinase by interaction with ras and by point mutation, EMBO Journal. 15: 2442-2451, 1996.
54. Rodriguez-Viciana, P., Warne, P., Khwaja, A., Marte, B., Pappin, D., Das, P., Waterfield, M., Ridley, A., and Downward, J. Role of Phosphoinositide 3-OH Kinase in Cell Transformation and Control of the Actin Cytoskeleton by Ras, Cell. 89: 457-467, 1997.
55. Welch, H., Eguinoa, A., Stephens, L., and Hawkins, P. Protein kinase B and Rac are activated in parallel within a phosphatidylinositide 3OH-kinase-controlled signaling pathway, The Journal of Biological Chemistry. 273: 11248-11256, 1998.
56. Sulciner, D., Irani, K., Yu, Z. -X., Ferrans, V., Goldschmidt-Clermont, P., and Finekl, T. rac1 Regulates a Cytokine-Stimulated Redox-Dependent Pathway Necessary for NF-kB Activation, Molecular and Cellular Biology. 16: 7115-7121, 1996.
57. Kane, L., Shapiro, V., Stokoe, D., and Weiss, A. Induction of NF-KB by the Akt/PKB kinase, Current Biology. 9: 601-604, 1999.
58. Westwick, J., Lambert, Q., Clark, G., Symons, M., Aelst, L., Pestell, R., and Der, C. Rac Regulation of Transformation, Gene Expression, and Actin Organization by Multiple, PAK-Independent Pathways, Molecular and Cellular Biology. 17: 1324-1335, 1997.
59. Gjoerup, O., Lukas, J., Bartek, J., and Willumsen, B. Rac and Cdc42 are potent stimulators of E2F-dependent transcription capable of promoting retinoblastoma susceptibility gene product hyperphosphorylation, The Journal of Biological Chemistry. 273: 18812-18818, 1998.
60. Page, K., Li, J., Hodge, J., Liu, P., Vanden Hoek, T., Becker, L., Pestell, R., Rosner, M., and Hershenson, M. Characterization of a rac1 signaling pathway to cyclin D1 expression in airway smooth muscle cells, The Journal of Biological Chemistry. 274: 22065-22071, 1999.
61. Joyce, D., Bouzahzah, B., Fu, M., Albanese, C., D'Amico, M., Steer, J., Klein, J., Lee, R., Segall, J., Westwick, J., Der, C., and Pestell, R. Integration of rac-dependent regulation of cyclin D1 transcription through a nuclear factor-kB-dependent pathway, 1999.
62. Muise-Helmeericks, R., Grimes, H., Bellacosa, A., Malstrom, S., Tsichlis, P., and Rosen, N. Cyclin D expression is controlled post-transcriptionally via a phosphatidylinositol 3-kinase/Akt-dependent pathway, The Journal of Biological Chemistry. 273: 29864-29872, 1998.
63. Alroy, I. and Yarden, Y. The erbB signaling network in embryogenesis and oncogenesis: signal diversification through combinatorial ligand-receptor interactions, FEBS Letters. 410: 83-86, 1997.
64. Tzahar, E. and Yarden, Y. The erbB-2/HER2 oncogenic receptor of adenocarcinomas: from orphanhood to multiple stromal ligands, Biochimica et Biophysica Acta. 1377: M25-M37, 1998.
65. Graus-Porta, D., Beerli, R., Daly, J., and Hynes, N. ErbB-2, the preferred heterodimerization partner of all ErbB receptors, is a mediator of lateral signaling, The EMBO Journal. 16, No. 7: 1647-1655, 1997.
66. Pinkas-Kramarski, R., Soussan, L., Waterman, H., Levkowitz, G., Alroy, I., Klapper, L., Lavi, S., Seger, R., Ratzkin, B., Sela, M., and Yarden, Y. Diversification of neu differentiation factor and epidermal growth factor signaling by combinatorial receptor interactions, The EMBO Journal. 15, No. 10: 2452-2467, 1996.
67. Prigent, S. and Gullick, W. Identification of c-erbB-3 binding sites for phaosphatidyl-inositol 3'-kinase and SHC using an EGF recpetor/c-erbB-3 chimera, The EMBO Journal. 13: 2831-2841, 1994.
68. Fedi, P., Pierce, J., DiFiore, P., and Kraus, M. Efficient coupling with phosphatidylinositol 3-kinase, but not phospholipase Cg or GTPase-activating protein, distinguishes ErbB-3 signaling from that of other ErbB/EGFR family members, Molecular and Cellular Biology. 14: 492-500, 1994.
69. Soltoff, S., Carraway III, K., Prigent, S., Gullick, W., and Cantley, L. ErbB3 is involved in activation of phosphatidylinositol 3-kinase by epidermal growth factor, Molecular and Cellular Biology. 14: 3550-3558, 1994.
70. Alimandi, M., Romano, A., Curia, M., Muraro, R., Fedi, P., Aaronson, S., Di Fiore, P., and Kraus, M. Cooperative signaling of ErbB3 and ErbB2 in neoplastic transformation and human mammary carcinomas, Oncogene. 10: 1813-1821, 1995.
71. Ram, T. and Ethier, S. Phosphatidylinositol 3-kinase recruitment by p185erbB-2 and erbB-3 is potently induced by neu differentiation factor/heregulin during mitogenesis and is constitutively elevated in growth factor-independent breast carcinoma cells with c-erbB-2 amplification, Cell Growth & Differentiation. 7: 551-561, 1996.

72. Zhang, H., Hannon, G., and Beach, D. p21-containing cyclin kinases exist in both active and inactive states, Genes & Development. 8: 1750-1758, 1994.
73. LaBaer, J., Garrett, M., Stevenson, L., Slingerland, J., Sandhu, C., Chou, H., Fattaey, A., and Harlow, E. New functional activities for the p21 family of CDK inhibitors, Genes & Development. 11: 847-862, 1997.
74. Cheng, M., Olivier, P., Diehl, J., Fero, M., Roussel, M., Roberts, J., and Sherr, C. The p21Cip1 and p27Kip1 CDK 'inhibitors' are essential activators of cyclin D-dependent kinases in murine fibroblasts, The EMBO Journal. 18: 1571-1583, 1999. 75. Canman, C., Gilmer, T., Coutts, S., and Kastan, M. Growth factor modulation of p53-mediated growth arrest versus apoptosis, Genes & Development. 9: 600-611, 1995.
76. Hiyama, H., Iavarone, A., and Reeves, S. Regulation of the cdk inhibitor p21 gene during cell cycle progression is under the control of the transcription factor E2F, Oncogene. 16: 1513-1523, 1998.
77. Lee, C. -W., Sorensen, T., Shikama, N., and La Thangue, N. Functional interplay between p53 and E2F through co-activator p300, Oncogene. 16: 2695-2710, 1998.
78. Gartel, A., Najmabadi, F., Goufman, E., and Tyner, A. A role for E2F1 in Ras activation of p21 (WAF1/CIPI) transcription, Oncogene. 19: 961-964, 2000.
79. Liu, Y., Martindale, J., Gorospe, M., and Holbrook, N. Regulation of p21 WAF1/CIP1 expression through mitogen-activated protein kinase signaling pathway, Cancer Research. 56: 31-35, 1996.
80. Lloyd, A., Obermuller, F., Staddon, S., Barth, C., McMahon, M., and Land, H. Cooperating oncogenes converge to regulate cyclin/cdk complexes, Genes & Development. 11: 663-677, 1997.
81. Pumiglia, K. and Decker, S. Cell cycle arrest mediated by the MEK/mitogen-activated protein kinase pathway, Proceedings of the National Academy of Sciences USA. 94: 448-452, 1997.
82. Serrano, M., Lin, A., McCurrach, M., Beach, D., and Lowe, S. Oncogenic ras provokes premature cell senescence associated with accumulation of p53 and p16INK4a, Cell. 88: 593-602, 1997.
83. Wagner, A., Kokontis, J., and Hay, N. Myc-mediated apoptosis requires wild-type p53 in a manner independent of cell cycle arrest and the ability of p53 to induce p21waf1/cip1, Genes & Development. 8: 2817-2830, 1994.
84. Packham, G., Porter, C., and Cleveland, J. c-Myc induces apoptosis and cell cycle progression by separable, yet overlapping, pathways, Oncogene. 13: 461-469, 1996.
85. Attardi, L., Lowe, S., Brugarolas, J., and Jacks, T. Transcriptional activation by p53, but not induction of the p21 gene, is essential for oncogene-mediated apoptosis, The EMBO Journal. 15: 3693-3701, 1996.
86. Miyashita, T. and Reed, J. Tumor suppressor p53 is a direct transcriptional activator of the human bax gene, Cell. 80: 293-299, 1995.
87. Buckbinder, L., Talbott, R., Velasco-Miguel, S., Takenaka, I., Faha, B., Seizinger, B., and Kley, N. Induction of the growth inhibitor IGF-binding protein 3 by p53, Nature. 377: 646-649, 1995.
88. Polyak, K., Xia, Y., Zweler, J., Kinzler, K., and Vogelstein, B. A model for p53-induced apoptosis, Nature. 389: 300-305, 1997.
89. Haupt, Y., Rowan, S., Shalian, E., Vousden, K., and Oren, M. Induction of apoptosis in HeLa cells by trans-activation-deficient p53, Genes & Development. 9: 2170-2183, 1995.
90. Wu, X. and Levine, A. p53 and E2F-1 cooperate to mediate apoptosis, Proc. Natl. Acad. Sci. USA. 91: 3602-3606, 1994.
91. Sakamuro, D., Eviner, V., Elliott, K., Showe, L., White, E., and Prendergast, G. c-Myc induces apoptosis in epithelial cells by both p53-dependent and p53-independent mechanisms, Oncogene. 11: 2411-2418, 1995.
92. Zindy, F., Eischen, C., Randle, D., Kamijo, T., Cleveland, J., Sherr, C., and Roussel, M. Myc signaling via the ARF tumor suppressor regulates p53-dependent apoptosis and immortalization, Genes & Development. 12: 2424-2433, 1998.
93. Prendergast, G. Mechanisms of apoptosis by c-Myc, Oncogene. 18: 2967-2987, 1999.
94. Kennedy, S., Wagner, A., Conzen, S., Jordan, J., Bellacosa, A., Tsichlis, P., and Hay, N . The PI 3-kinase/Akt signaling pathway delivers an anti-apoptotic signal, Genes & Development. 11: 703-713, 1997.
95. Khwaja, A., Rodriguez-Viciana, P., Wennstrom, S., Warne, P., and Downward, J. Matrix adhesion and Ras transformation both activate a phosphoinositide 3-OH kinase and protein kinase B/Akt cellular survival pathway, The EMBO Journal. 16, No. 10: 2783-2793, 1997.
96. Kauffmann-Zeh, A., Rodriguez-Viciana, P., Ulrich, E., Gilbert, C., Coffer, P., Downward, J., and Evan, G. Suppression of c-Myc-induced apoptosis by ras signalling through PI(3)K and PKB, Nature. 385: 544-548, 1997.
97. Datta, S., Dudeck, H., Tao, X., Masters, S., Fu, H., Gotoh, Y., and Greenberg, M. Akt phosphorylation of BAD couples survival signals to the cell-intrinsic death machinery, Cell. 91: 231-241, 1997.
98. Bertrand, F., Atfi, A., Cadoret, A., L'Allemain, G., Robin, H., Lascols, O., Capeau, J., and Cherqui, G. A role for Nuclear Factor kB in the antiapoptotic function of insulin, The Journal of Biological Chemistry. 273: 2931-2938, 1998.
99. Ravi, R., Mookerjee, B., van Hensbergen, Y., Bedi, G., Giordano, A., El-Deiry, W., Fuchs, E., and Bedi, A. p53-mediated repression of nuclear factor-kB RelA via the transcriptional integrator p300, Cancer Research. 58: 4531-4536, 1998.
100. Webster, G. and Perkins, N. Transcriptional Cross Talk between NF-kB and p53, Molecular and Cellular Biology. 19: 3485-3495, 1999.
101. Bates, S. and Vousden, K. Mechanisms of p53-mediated apoptosis, Cellular and Molecular Life Sciences. 55: 28-37, 1999.
102. Toi, M., Inada, K., Suzuki, H., and Tominaga, T. Tumor angiogenesis in breast cancer: its importance as a prognostic indicator and association with vascular endothelial growth factor expression, Breast Cancer Research and Treatment. 36: 193-204, 1995.
103. Gasparini, G., Toi, M., Gion, M., Verdiero, P., Dittadi, R., Hanatani, M., Matsubara, I., Vinante, O., Bonoldi, E., Boracchi, P., Gatti, C., Suzuki, H., and Tominaga, T. Prognostic significance of vascular endothelial growth factor protein in node-negative breast carcinoma, Journal of the National Cancer Institute. 89: 139-147, 1997.
104. Eppenberger, U., Kueng, W., Schlaeppi, J. -M., Roesel, J., Benz, C., Mueller, H., Matter, A., Zuber, M., Luescher, K., Litchgi, M., Scmitt, M., Foekens, J., and Eppenberger-Castori, S. Markers of tumor angiogenesis and proteolysis 104. (continued) independently define high- and low-risk subsets of node-negative breast cancer patients, Journal of Clinical Oncology. 16: 3129-3136, 1998.

105. Linderholm, B., Tavelin, B., Grankvist, K., and Henriksson, R. Vascular endothelial growth factor is of high prognostic value in node-negative breast carcinoma, Journal of Clinical Oncology. 16: 3121-3128, 1998.

106. Linderholm, B., Lindh, B., Tavelin, B., Grankvist, B., and Henriksson, R. p53 and vascular-endothelial-growth-factor (VEGF) expression predicts outcome in 833 patients with primary breast carcinoma, International Journal of Cancer. 89: 51-62, 2000.

107. Brown, L., Berse, B., Jackman, R., Topgnazzi, K., Guidi, A., Dvorak, H., Senger, D., Connolly, J., and Schnitt, S. Expression of vascular permeability factor (Vascular Endothelial Growth Factor) and its receptors in breast cancer, Human Pathology. 26: 86-91, 1995.

108. Obermair, A., Kucera, E., Mayerhofer, K., Speiser, P., Seifert, M., Czerwenka, K., Kaider, A., Leodolter, S., Kainz, C., and Zeillinger, R. Vascular endothelial growth factor (VEGF) in human breast cancer: correlation with disease-free survival, International Journal of Cancer. 74: 455-458, 1997.

109. Viloria Petit, A., Rak, J., Hung, M. -C., Rockwell, P., Goldstein, N., Fendly, B., and Kerbel, R. Neutralizing antibodies against epidermal growth factor and erbb-2/neu receptor tyrosine kinases down-regulate vascular endothelial growth factor production by tumor cells in vitro and in vivo, American Journal of Pathology. 151: 1523-1530, 1997.

110. Feldkamp, M., Lau, N., Rak, J., Kerbel, R., and Guha, A. Normoxic and hypoxic regulation of vascular endothelial growth factor (VEGF) by astrocytoma cells is mediated by ras, International Journal of Cancer. 81: 118-124, 1999.

111. Grugel, S., Finkenzeller, G., Weindel, K., Barleon, B., and Marme, D. Both v-Ha-Ras and v-Raf stimulate expression of the vascular endothelial growth factor in NIH 3T3 cells, The Journal of Biological Chemistry. 270, No. 43: 25915-25919, 1995.

112. Larcher, F., Robles, A., Duran, H., Murillas, R., Quintanilla, M., Cano, A., Conti, C., and Jorcano, J. Up-regulation of vascular endothelial growth factor/vascular permeability factor in mouse skin carcinogenesis correlates with malignant progression state and activated H-ras expression levels, Cancer Research. 56: 5391-5396, 1996.

113. Rak, J., Mitsuhashi, Y., Sheehan, C., Tamir, A., Viloria-Petit, A., Filmus, J., Mansour, S., Ahn, N., and Kerbel, R. Oncogenes and Tumor Angiogenesis: Differential Modes of Vascular Endothelial Growth Factor Up-Regulation in ras-transformed Epithelial Cells and Fibroblasts, Cancer Research. 60: 490-498, 2000.

114. Mazure, N., Chen, E., Laderoute, K., and Giacca, A. Induction of vascular endothelial growth factor by hypoxia is modulated by a phosphotidylinositol 3-kinase/Akt signaling pathway in Ha-ras-transformed cells through a hypoxia inducible factor-1 transcriptional element, Blood. 90: 3322-3331, 1997.

115. Klapper, L., Glathe, S., Vaisman, N., Hynes, N., Andrews, G., Sela, M., and Yarden, Y. The erbB-2/Her2 oncoprrotein of human carcinomas may function solely as a shared coreceptor for multiple stroma-derived growth factors, Proceedings of the National Academy of Sciences USA. 96: 4995-5000, 1999.

116. Naidu, R., Yadav, M., Nair, S., and Kutty, M. Expression of c-erbB-3 protein in primary breast carcinomas, British Journal of Cancer. 78: 1385-1390, 1998.

117. Wallasch, C., WeilB, F., Niederfellner, G., Jallal, B., Issing, W., and Ullrich, A. Heregulin-dependent regulation of HER2/neu oncogenic signaling by heterodimerization with HER3, The EMBO Journal. 14, No. 17: 4267-4275, 1995.

118. Gershtein, E., Shatskaya, V., Ermilova, V., Kushlinsky, N., and Krasilnikov, M. Phosphatidylinositol 3-kinase expression in human breast cancer, Clinica Chimica Acta. 287: 59-67, 1999.

119. Fritz, G., Just, I., and Kaina, B. Rho GTPases are over-expressed in human tumors, International Journal of Cancer. 81: 682-687, 1999.

120. Sovak, M., Bellas, R., Kim, D., Zanieski, G., Rogers, A., Traish, A., and GE, S. Aberrant Nuclear Factor-kB/Re1 expression and the pathogenesis of breast cancer, Journal of Clinical Investigation. 100: 2952-2960, 1997.

121. Nakshatri, H., Bhat-Nakshatri, P., Martin, D., Goulet, R. J., and Sledge, G. J. Constitutive activation of NF-kB during progression of breast cancer to hormone-independent growth, Molecular and Cellular Biology. 17: 3629-3639, 1997.

122. Oyama, T., Kashiwabara, K., Yoshimoto, K., Arnold, A., and Koerner, F. Frequent overexpression of the cyclin D1 oncogene in invasive lobular carcinoma of the breast, Cancer Research. 58: 2876-2880, 1998.

123. Hashizume, R., Koizzumi, H., Ihara, A., Ohta, A., and Uchikoshi, T. Expression of b-catenin in normal breast tissue and breast carcinoma: a comparative study with epithelial cadherin and a-catenin, Histopathology. 29: 139-146, 1996.

124. De Leeuw, W., Berx, G., Vos, C., Peterse, J., Van de Vijer, M., Litvinov, S., Van Roy, F., Cornelisse, C., and Cleton-Jansen, A. -M. Simultaneous loss of E-cadherin and catenins in invasive lobular breast cancer and lobular carcinoma in situ, Journal of Pathology. 183: 404-411, 1997.

125. Bukholm, I., Nesland, J., Karesen, R., Jacobsen, U., and Borresen-Dale, A. L. E-cadherin an a-, b-, and g-catenin protein expression in relation to metastasis in human breast carcinoma, Journal of Pathology. 185: 262-266, 1998.

126. Bankfalvi, A., Terpe, H. -J., Breukelmann, D., Bier, B., Rempe, D., Pschadka, G., Krech, R., Lelle, R. -J., and Boecker, W. Immunophenotypic and prognostic analysis of E-cadherin and b-catenin expression during breast carcinogenesis and tumor progression: a comparative study with CD44, Histopathology. 34: 25-34, 1999.

127. Barnes, D. and Gillett, C. Cyclin D1 in breast cancer, Breast Cancer Research and Treatment. 52: 1-15, 1998.

128. Ilyas, M. and Tomlinson, I. The interactions of APC, E-cadherin, and b-catenin in tumour development and progression, Journal of Pathology. 182: 128-137, 1997.

129. Berx, G., Nollet, F., and Van Roy, F. Dysregulation of the E-cadherin/catenin complex by irreversible mutations in human carcinomas, Cell Adhesion and Communication. 6: 171-184, 1998.

130. Oyama, T., Kanai, Y., Ochiai, A., Akimoto, S., Oda, T., Yanagihara, K., Nagafuchi, A., Tsukita, S., Shibamoto, S., and Ito, F. A truncated beta-catenin disrupts the interaction between E-cadherin and alpha-catenin: a cause of loss of intercellular afhesiveness in human cancer cells lines, Cancer research. 54: 6282-6287.

131. Morin, P. b-catenin signaling and cancer, BioEssays. 21: 1021-1030, 1999.

132. Kikuchi, A. Regulation of b-catenin signaling in the Wnt pathway, Biochemical and Biophysical Research Communications. 268: 243-248, 2000.

133. Kamentsky, L., Burger, D., Gershman, R., Kamentsky, L., and Luther, E. Slide-based laser scanning cytometry, Acta Cytologica. 41: 123-143, 1997.
134. Pollice, A., McCoy, J., J P, Shackney, S., Smith, C., Agarwal, J., Burholt, D., Janocko, L., Hornicek, F., Singh, S., and Hartsock, R. Sequential paraformaldehyde and methanol fixation for simultaneous flow cytometric analysis of DNA, cell surface proteins, and intracellular proteins, Cytometry. 13: 432-444, 1992.
135. Pollice, A., Smith, C., K, B., Farkas, D., Silverman, J., and Shackney, S. Multiparameter analysis of human epithelial tumors by laser scanning cytometry, submitted for publication, 2000.
136. Norton, L. A gompertzian model of human breast cancer growth, Cancer Research. 48: 7067-7071, 1988.

What is claimed is:

1. A method for determining a likelihood of cancer recurrence in a patient with cancer comprising the steps of:

obtaining cells from a cancerous tumor in the patient;

performing simultaneously multiple correlated measurements on each cell to obtain cell data for each cell regarding each cell's place in a genetic evolutionary pathway that had occurred in the tumor due to an accumulation of genetic abnormalities within each cell;

reading the data into an array in memory, where rows of the array represent the data for individual tumor cells and columns of the array represent different measurements performed on each cell;

identifying the genetic evolutionary pathway of each cell by processing the data in the array with a computer;

recognizing distinctive false negative patterns from the cell data and its genetic evolutionary pathway; and correlating the false negative patterns to aberrations in mitogenic signaling to determine a likelihood of recurrence of the cancer in the patient.

* * * * *